US012727920B2

(12) United States Patent
Hills

(10) Patent No.: US 12,727,920 B2
(45) Date of Patent: Sep. 8, 2026

(54) SPINAL TREATMENT DEVICES, SYSTEMS AND METHODS

(71) Applicant: Christopher C. Hills, Jackson, WY (US)

(72) Inventor: Christopher C. Hills, Jackson, WY (US)

( * ) Notice: Subject to any disclaimer, the term of this patent is extended or adjusted under 35 U.S.C. 154(b) by 0 days.

(21) Appl. No.: 19/232,526

(22) Filed: Jun. 9, 2025

(65) Prior Publication Data

US 2026/0047870 A1 Feb. 19, 2026

Related U.S. Application Data

(60) Provisional application No. 63/658,280, filed on Jun. 10, 2024.

(51) Int. Cl.

*A61B 17/70* (2006.01)
*A61B 17/56* (2006.01)
*A61B 90/00* (2016.01)

(52) U.S. Cl.

CPC ...... *A61B 17/7022* (2013.01); *A61B 17/7032* (2013.01); *A61B 90/03* (2016.02); *A61B 2017/564* (2013.01); *A61B 2090/033* (2016.02)

(58) Field of Classification Search

CPC ............ A61B 17/7022; A61B 17/7032; A61B 2017/0414

See application file for complete search history.

(56) References Cited

U.S. PATENT DOCUMENTS 6,086,590 A * 7/2000 Margulies ............ A61B 17/842 606/279
6,514,255 B1 * 2/2003 Ferree ................ A61B 17/8861 606/76
10,238,433 B2 * 3/2019 Belliard ............. A61B 17/7053
10,463,403 B2 11/2019 Mickiewicz et al.
12,171,465 B2 12/2024 Gordon
12,201,328 B2 * 1/2025 Lengyel ............. A61B 17/7032
2008/0125779 A1 * 5/2008 Ferree ................ A61B 17/0401 606/246
2008/0125780 A1 * 5/2008 Ferree ................ A61B 17/0401 606/86 R
2008/0125813 A1 * 5/2008 Erickson ............ A61B 17/7032 606/279
2009/0024165 A1 * 1/2009 Ferree ................ A61B 17/7022 606/264

(Continued)

*Primary Examiner* — Jacqueline T Johanas
(74) *Attorney, Agent, or Firm* — Foley & Lardner LLP

(57) ABSTRACT

Devices, systems, and methods for treating a spinal condition are disclosed that include a tulip to secure to a rod and an orthopedic screw including an eyelet. The tulip includes a housing that provides a rod channel to receive the rod therethrough and a threaded conduit of a clamping mechanism, which is to secure the rod within the rod channel. The orthopedic screw is at the clamping mechanism to secure the rod at the tulip. Tightening the orthopedic screw tightens the clamping mechanism. The orthopedic screw includes an elongate threaded cylindrical shaft to be rotated into the threaded conduit of the tulip housing to engage and mate with the threaded conduit of the clamping mechanism. The orthopedic screw includes a head to be manipulated to rotate the threaded cylindrical shaft into the threaded conduit of the tulip. The head includes an eyelet to receive a tether therethrough.

22 Claims, 10 Drawing Sheets

(56) References Cited

U.S. PATENT DOCUMENTS

2009/0030466 A1* 1/2009 Strauss .............. A61B 17/7059 606/301
2009/0131982 A1 5/2009 Schwab
2010/0211075 A1* 8/2010 Stone .................. A61B 17/683 606/281
2013/0110173 A1* 5/2013 Carls ..................... A61B 17/70 606/301
2014/0094851 A1* 4/2014 Gordon .............. A61B 17/7055 606/264
2015/0201973 A1* 7/2015 Lindemann ........ A61B 17/7053 606/279
2016/0324547 A1* 11/2016 Miller ................ A61B 17/7032
2018/0078286 A1* 3/2018 Le Couëdic ....... A61B 17/7049
2018/0353217 A1* 12/2018 Rice .................. A61B 17/8869
2019/0029733 A1 1/2019 Mickiewicz et al.
2019/0142472 A1* 5/2019 Mire ..................... A61B 17/70 606/279
2019/0290329 A1* 9/2019 Bess .................. A61B 17/7023
2019/0290334 A1* 9/2019 Prygoski .............. A61B 17/809
2020/0000505 A1* 1/2020 Vitale .................. A61B 17/842
2020/0085471 A1* 3/2020 McClintock ....... A61B 17/8625
2020/0170696 A1* 6/2020 Haber ................ A61B 17/7044
2021/0121204 A1* 4/2021 Murray ................ A61B 17/707
2021/0275228 A1 9/2021 Mire et al.
2022/0031301 A1* 2/2022 Rippe ................ A61B 17/0401
2022/0280199 A1* 9/2022 Chen .................... A61B 17/683
2023/0293206 A1* 9/2023 Mundis, Jr. ........ A61B 17/7053 606/279
2023/0310040 A1* 10/2023 Braun ................ A61B 17/0401 606/263
2024/0023996 A1* 1/2024 Albert ................ A61B 17/8685
2025/0261971 A1* 8/2025 Mast .................. A61B 17/8869
2026/0020883 A1* 1/2026 Kondrashov ...... A61B 17/1728
2026/0047870 A1* 2/2026 Hills .................. A61B 17/7022

* cited by examiner

SPINAL TREATMENT DEVICES, SYSTEMS AND METHODS

RELATED APPLICATIONS

This application claims the benefit of priority under 35 U.S. C. § 119(e) to U.S. Provisional Patent Application 63/658,280, titled "SPINAL TREATMENT DEVICES, SYSTEMS AND METHODS," filed Jun. 10, 2024, which is hereby incorporated herein by reference in its entirety.

TECHNICAL FIELD

The present disclosure relates generally to medical devices, systems, and methods. More particularly, the present disclosure is directed to devices, systems, and methods used in orthopedic procedures for treatment of spinal disorders in patients.

BRIEF DESCRIPTION OF THE DRAWINGS

The present embodiments will become more fully apparent from the following description and appended claims, taken in conjunction with the accompanying drawings. Understanding that the accompanying drawings depict only typical embodiments, and are, therefore, not to be considered limiting of the scope of the disclosure, the embodiments will be described and explained with reference to the accompanying drawings.

DETAILED DESCRIPTION

Figure 1:
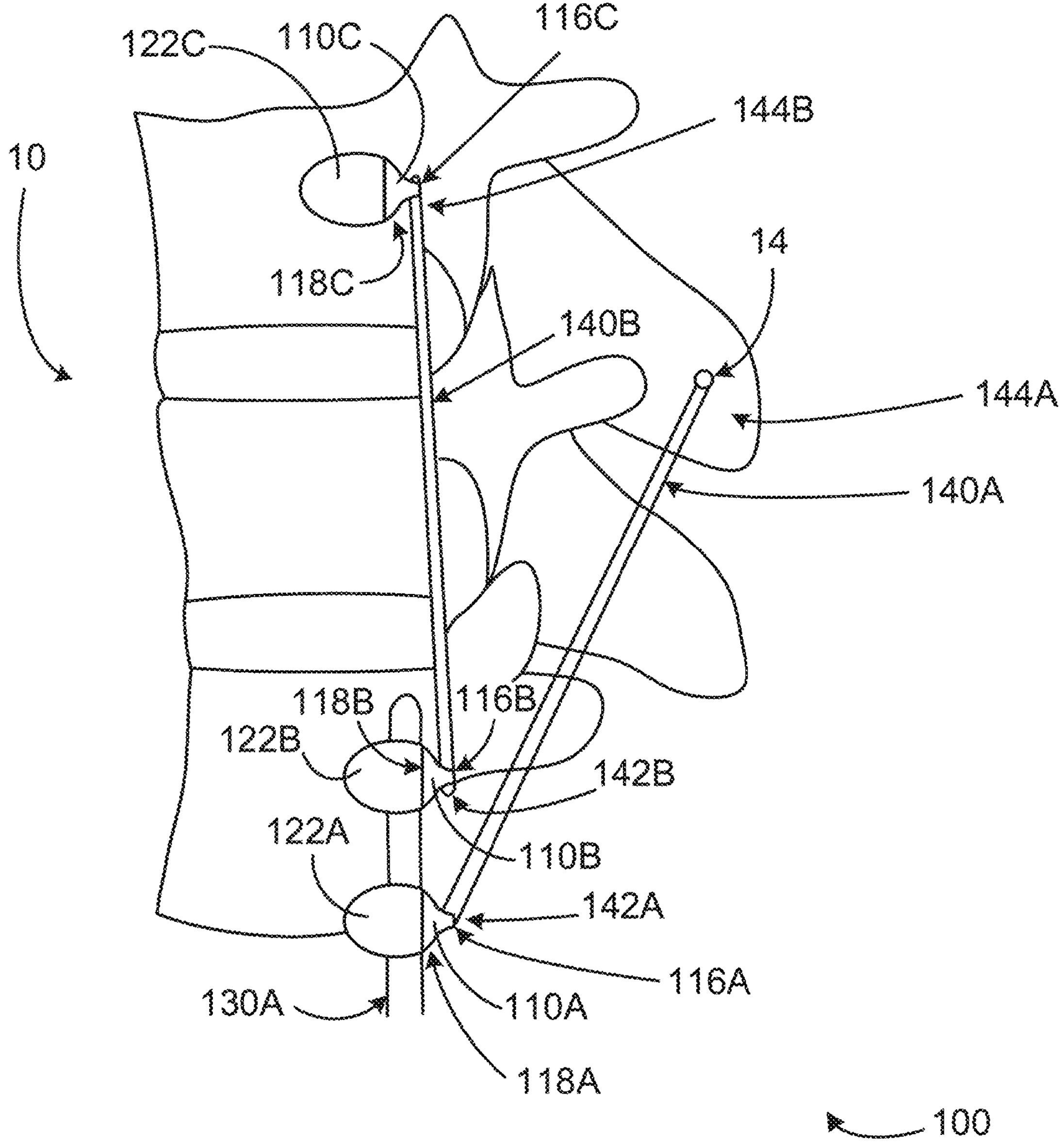
FIG. 1 is a lateral view of the anatomy and placement of an orthopedic system for treating a spinal condition, according to one embodiment of the present disclosure.

Proximal Junctional Kyphosis (PJK) is a condition that commonly occurs after a spinal fusion surgery, particularly in the thoracolumbar region. PKJ is characterized by an abnormal forward curvature of the spine (e.g., kyphosis) at the junctional area where fused and unfused segments of the spine meet. This condition can cause pain, functional limitations, and in severe cases, neurological deficits.

Some factors that can contribute to the development of PJK include the surgical technique (e.g., approach, number of fused segments, instrumentation used, and alignment achieved during or by the technique), patient factors (e.g., age, bone density, body mass index (BMI), and pre-existing spinal deformity), biomechanical stress (e.g., alterations in spinal biomechanics resulting from the fusion surgery), bone quality and density (e.g., poor bone quality and density can affect the stability of the fused segments and increase the risk of adjacent segment degeneration).

Spine surgeons can utilize medical devices (e.g., implants) to avert or address Proximal Junctional Kyphosis (PJK), either as standalone interventions or as components of surgical procedures. Commonly used devices and/or techniques to treat a spinal disorder include adding bone cement to the upper instrumented vertebrae (vertebroplasty) to minimize the risk of vertebral body fracture; softening the transition vertebrae from instrumented to un-instrumented levels with hooks instead of a more rigid pedicle screw construct (e.g., one or more pedicle screws used to physically secure one or more rods, which are secured with tulips that are physically attached to the pedicle screws); and using one or more tethers between one or more portions of the spine, which may buffer the transitional stresses between different portions of the spine (e.g., between a portion of the spine that is coupled to a rigid pedicle screw construct and a portion of the spine that is located above, and is not coupled to, the rigid construct).

One common application of a tether to treat a spinal disorder includes wrapping the tether underneath a pedicle screw and rod construct and weaving the tether through the spinous process. This construct, however, does not provide a mechanical lever arm that appropriately counter-balances the main kyphotic disposition of a spinal deformity and it can rely on the relatively low marginal bone strength of the spinous process (e.g., the spinous process does not often possess the marginal bone strength required to secure the tether and/or spine as desired).

It will be readily understood that the components of the embodiments as generally described and illustrated in the figures herein could be arranged and designed in a wide variety of different configurations. Thus, the following more detailed description of various embodiments, as represented in the figures, is not intended to limit the scope of the disclosure, as claimed, but is merely representative of various embodiments. While the various aspects of the embodiments are presented in drawings, the drawings are not necessarily drawn to scale unless specifically indicated.

FIG. 1 is a lateral view of the anatomy and placement of an orthopedic system 100 for treating a spinal condition, according to one embodiment of the present disclosure. The orthopedic system 100 is shown with a spine 10. The orthopedic system 100 can include an orthopedic screw 118A, which can include a first cylindrical shaft 110A and a first eyelet 116A. The orthopedic system 100 can include a first tulip 122A. The first tulip 122A may be a universal tulip, which is configured to engage and/or secure to a rod 130A that may be installed (e.g., via pedicle screws) at the spine 10. The first cylindrical shaft 110A and the first tulip 122A may be configured to retain and/or secure to the rod 130A, potentially with one or more additional components (e.g., one or more additional tulips and one or more additional cylindrical shafts). The first cylindrical shaft 110A and the first tulip 122A may be configured to retain and/or secure the rod 130A, potentially with one or more additional components (e.g., one or more additional tulips and one or more additional cylindrical shafts).

In some embodiments, the rod 130A may be configured (e.g., positioned, secured, etc.) to maintain and/or support the position of one or more portions of the spine 10 (e.g., one or more vertebrae of a non-fused portion) relative to another portion of the spine 10 (e.g., one or more fused vertebrae forming a fused portion. Stated differently, the rod 130A may be used in or with the orthopedic system 100 to provide rigid physical support to one or more portions of the spine 10, including via one or more pedicle screws inserted into the spine 10 at one or more different locations relative to the spine 10 and secured (e.g., via one or more corresponding tulips) to the rod 130A. Additionally, in some embodiments, the orthopedic system 100 may include more than one rod and/or a different number of pedicle screws than shown in the embodiments illustrated in FIGS. 1-10.

As shown in FIG. 1, the first cylindrical shaft 110A and the first tulip 122A may be physically coupled together with the first cylindrical shaft 110A secured to at least a portion of the first tulip 122A. For example, the first tulip 122A may include a conduit having a helical inclined plane (e.g., female threads) to receive, and physically secure to the first cylindrical shaft 110A via a corresponding helical inclined plane (e.g., male threads) formed around or in a portion of the first cylindrical shaft 110A (e.g., a portion that is opposite the eyelet 116A). Stated otherwise, the first orthopedic screw 118A can be threaded (e.g., a helical inclined plane wrapping around an end of the first cylindrical shaft 110A) and configured to couple with (e.g., engage and mate with) the helical inclined plane (e.g., female threads) formed in the tulip 122A (e.g., in a conduit of the first tulip 122A).

The first eyelet 116A can be configured to receive and secure a first tether 140A at a first end 142A of the first tether 140A (e.g., by receiving a portion of the first tether 140A and/or the first end 142, which may be looped through the first eyelet 116A). The first eyelet 116A may secure the first end 142A of the tether 140A at a first point on or relative to the spine 10. The first point can be at or near a point of insertion of a pedicle screw on a portion of the spine 10 that has been treated, such as through a spinal fusion procedure. In the illustrated embodiment of FIG. 1, the first end 142 of the tether 140 is secured to the first eyelet 116A of the first orthopedic screw 118A received into the first tulip 122A (e.g., a universal tulip) at the first point. The first point is fixed relative to a vertebra of a fused portion of the spine 10.

The first tether 140A may further include a second end 144A that is secured at a second point 14 on the spine 10, or at a second location 14 relative to the spine 10. For example, and as shown in FIG. 1, the second end 144A of the first tether 140A may be secured to a second point 14 that is located at, or that is a part of, a portion of the spinous process of the spine 10. More specifically, the second end 144A of the first tether 140A may be secured to a hole in the spinous process (or any other portion of the spine 10 at which the second end 144A is secured) and/or to one or more pieces of orthopedic hardware located at and/or secured to the second point 14 of the spine 10. For example, the second end 144A may be secured to a grommet, a pedicle screw, an eyelet, and/or one or more other pieces of hardware located at the second point 14 of the spine 10. Additionally, the second point 14 of the spine 10 may be at another location relative to the spine 10 that differs from the location shown in FIG. 1. For example, the second point 14 may be located at a different portion of the spinous process or may be located proximate to one or more vertebrae instead of within a portion of a spinous process.

In some embodiments, the orthopedic system 100 can include a first pedicle screw, that is to be inserted into a vertebra of the spine 10 at a first point, and the first pedicle screw can include a first pedicle screw shaft and the first tulip 122A. The first pedicle screw shaft is to be screwed into a vertebra of the spine 10. The first tulip 122A is, or is at (or otherwise integrated with), a head of the first pedicle screw. The first cylindrical shaft 110A of the first orthopedic screw 118A and the first tulip 122A may be configured to retain and/or secure, potentially with one or more additional components (e.g., one or more additional tulips and one or more additional cylindrical shafts), a rod 130A.

The orthopedic system 100 can further include a second orthopedic screw 118B, which can include a second cylindrical shaft 110B, and a second eyelet 116B. The second eyelet 116B can be coupled to, and/or formed at an end of, the second cylindrical shaft 110B. The second tulip 122B may be physically coupled to, and/or formed as part of, a pedicle screw (e.g., a second pedicle screw not shown in FIG. 1, see, e.g., FIG. 2) that is secured to, and/or inserted at, a vertebra of the spine 10 that may be disposed at a distance from the location of the first tulip 122A.

As described above with reference to the first tulip 122A and the first cylindrical shaft 110A, the second tulip 122B and the second cylindrical shaft 110B may be configured to retain and/or secure the rod 130A, potentially along with one or more additional components (e.g., the first tulip 122A, the first cylindrical shaft 110A, and/or one or more additional components). As shown in FIG. 1, the second tulip 122B and the second cylindrical shaft 110B may retain and/or secure (e.g., come in physical contact with) a portion of the rod 130A that is disposed a distance from the portion of the rod 130A secured by the first tulip 122A and the first cylindrical shaft 110A.

As shown in FIG. 1, the second cylindrical shaft 110B of the second orthopedic screw 118B and the second tulip 122B may be physically coupled together, similar to the first tulip 122A and the first cylindrical shaft 110A of the first orthopedic screw 118A. For example, the second tulip 122B may be configured to receive, and physically secure to, the second cylindrical shaft 110B via a helical inclined plane (e.g., female threads) formed in a portion (e.g., a conduit) of the second tulip 122B, which is configured to couple with (e.g., engage and mate with) a corresponding helical inclined plane (e.g., male threads) formed in a portion of the second cylindrical shaft 110B. The helical inclined plane (e.g., male threads) may be formed in a portion of the second cylindrical shaft 110B that is opposite the portion at which the second eyelet 116B is formed.

The second eyelet 116B can be configured to receive and secure a second tether 140B at a first end 142B of the second tether 140B (e.g., by receiving a portion of the second tether 140B and/or of the first end 142B, which may be looped through the eyelet 116B). The second eyelet 116B may secure the first end 142B of the tether 140B at a third point on the spine 10, or at a third location relative to the spine 10 (e.g., a third location that is disposed a vertical distance above the location where the first tether 140A is secured to the first eyelet 116A). The second tether 140B may further include a second end 144B that is secured at a fourth point on the spine 10, or at a fourth location relative to the spine 10 (e.g., the location of another pedicle screw and/or eyelet 116C).

For example, and as shown in FIG. 1, a second end 144B of the second tether 140B may be secured to a third eyelet 116C that is located at, or that is a part of, a fourth location (e.g., portion and/or vertebrae) of the spine 10. The third eyelet 116C may be part of a third orthopedic screw 118C, which may include a third cylindrical shaft 110C and which may be substantially similar to the other orthopedic screws 118 of the orthopedic system 100 (e.g., the first orthopedic screw 118A and the second orthopedic screw 118B). The third cylindrical shaft 110C may be physically coupled with (e.g., secured to) a third tulip 122C. The third tulip 122C may be substantially similar to the first and second tulips 122A and 122B described above.

For example, the third tulip 122C may be coupled to, and/or part of, a third pedicle screw that is inserted into a portion of the spine 10 (e.g., a portion of the vertebrae proximate to the third tulip 122C in FIG. 1). However, as shown in FIG. 1, the third tulip 122C may be physically coupled to the third cylindrical shaft 110C (e.g., via a helical inclined plane of the tulip 122C and a corresponding helical incline plane formed in the third cylindrical shaft 110C) and not to any portion of a rod (e.g., rod 130A). As also shown in FIG. 1, the second end 144B of the second tether 140B may be secured to the third eyelet 116C that is located at a portion of the spine 10 disposed a substantially vertical distance from the location of the second eyelet 116B (e.g., a fourth location and/or a fourth portion of the spine 10).

As described herein, the tethers (e.g., the first tether 140A and the second tether 140B) may be formed from a material suitable for use in an orthopedic procedure. For example, the tether(s) 140 (e.g., the first and second tethers 140A, 140B and/or one or more additional tether(s) not shown in FIG. 1) may be formed from MERSILENE® tape, a polyester fiber, and/or any material suitable for use as a tether in an orthopedic procedure. Together, the first and second tethers 140A, 140B may be configured to prevent, inhibit, and/or substantially reduce, an amount of forward movement by a portion of the spine 10 (e.g., by the positions of the first 142A, 142B and second ends 144A, 144B of the tethers 140A, 140B and/or the tension(s) present in the tethers 140A, 140B). For example, the tethers 140A, 140B, and the hardware to which each tether 140 is secured, may be configured to reduce and/or inhibit an amount of forward movement by the portion of the spine 10 illustrated in FIG. 1. In some embodiments, the portion of the spine 10 illustrated in FIG. 1 may be an unfused portion of the spine 10 (e.g., one or more unfused vertebrae), which may be disposed above a fused portion of the spine 10 and/or one or more fused vertebrae of the spine 10 (e.g., one or more vertebrae that have been fused to treat a spinal condition).

In some embodiments, the first ends 142A, 142B of the first and second tethers 140A, 140B may both be fastened to a single eyelet, including, for example, the first eyelet 116A, the second eyelet 116B, and/or one or more other eyelets positioned to be secured to one or more tethers. Accordingly, in some embodiments, an eyelet coupled to a tulip (e.g., the first eyelet 116A) may be configured (e.g., sized, shaped, positioned, etc.) to receive more than one tether therethrough, which may include threading a plurality of tethers through a single eyelet coupled to a single tulip (e.g., threading the first ends 142A, 142B of the first and second tethers 140A, 140B through the same eyelet).

Additionally, in some embodiments, each eyelet of an orthopedic system may be configured to provide and/or to facilitate a specific angle of a corresponding tether secured to the eyelet(s). For example, in some embodiments, an eyelet, and a corresponding hole in the spine (e.g., in the spinous process) or a location of a corresponding orthopedic component, may be configured to secure a tether at an angle equal to, substantially equal to, and/or that is approximately, 45 degrees with respect to a horizontal plane located at the position of the eyelet. Similarly, in some embodiments, one or more eyelets and/or other components may be configured (e.g., sized, positioned, oriented, etc.) to provide an angle to a tether that is between 40 and 50 degrees with respect to a horizontal plane located at the position of the eyelet to which one end of the tether is coupled.

As can also be appreciated, although the foregoing discussion describes first and second ends of tethers each secured at or to different eyelets, in other embodiments the first end of a tether can be secured at a first eyelet, the tether can then extend through a second eyelet and loop back to the first eyelet. In still other embodiments the first end of a tether can be secured at a first eyelet, the tether can then extend through a second eyelet and loop back to a third eyelet. Stated otherwise, one or more tethers of an orthopedic system can be configured and arrange in relation to eyelets, whether by securement (e.g., tying) or by passing through (e.g., looping through) as may provide appropriately arranged forces on an unfused portion of the spine.

Figure 2:
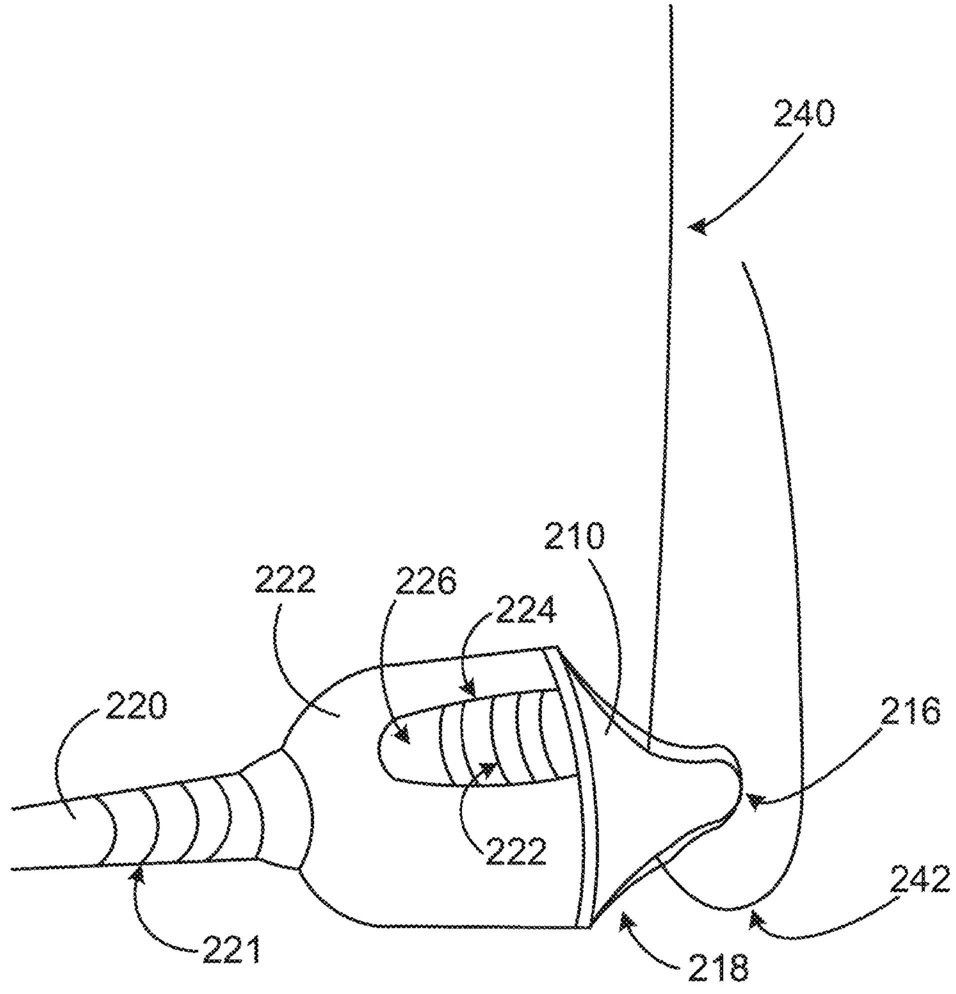
FIG. 2 is an orthopedic system for treating a spinal condition, according to one embodiment of the present disclosure.

FIG. 2 is an orthopedic system 200 for treating a spinal condition, according to one embodiment of the present disclosure. The orthopedic system 200 is configured to be secured to at least a portion of a spine. The orthopedic system 200 can include an orthopedic screw 218. The orthopedic system 200 can include a pedicle screw 220 with a tulip 222. The orthopedic system 200 can include a tether 240.

The orthopedics screw 218 can include a cylindrical shaft 210 and an eyelet 216. The orthopedic screw 218, and specifically the cylindrical shaft 210, is configured to couple to the tulip 222 of the pedicle screw 220. As shown in FIG. 2, the tulip 222 is coupled to, and/or physically connected to, at least a portion of a pedicle screw 220 (e.g., an end portion of the shaft of the pedicle screw 220). The pedicle screw 220 can include a plurality of threads 221, or a helical inclined plane, that wrap around a shaft of the pedicle screw 220 and are configured to secure the pedicle screw 220 to a portion of a patient's spine (e.g., to secure the pedicle screw 220 at a location on the spine). The orthopedic system 200 can be secured to the spine via the pedicle screw 220.

As described previously, the cylindrical shaft 210 and the tulip 222 may be configured to retain and/or secure at least a portion of a rod (not shown, see, e.g., the rod 130A shown in FIG. 1). For example, the tulip 222 may be configured with a channel 226 that is configured (e.g., sized, shaped, etc.) to physically receive and/or couple with a rod or portion thereof (e.g., the rod 130A described above with reference to FIG. 1). Additionally, the cylindrical shaft 210 may be configured to couple with the tulip 222, including at a conduit 224 formed by the tulip 222 and configured to receive the cylindrical shaft 210. The cylindrical shaft 210 may be configured to engage and/or physically contact a portion of a rod disposed within the channel 226 of the tulip 222. Accordingly, the tulip 222 and the cylindrical shaft 210 may be configured to physically couple in a way that can secure a rod, or a portion thereof, for use in the orthopedic system 200 (e.g., to provide rigid physical support to one or more portions of the spine of a patient).

The system 200 is configured to be secured to at least a portion of a patient's spine. For example, the pedicle screw 220, or at least a portion thereof, is configured to insertion into a patient's spine. More specifically, the pedicle screw 220 is configured to be anchored in a portion of a patient's spine (e.g., a vertebra). Some embodiments of the orthopedic systems disclosed herein can include a plurality of pedicle screws that can each be anchored to a different portion of a patient's spine (e.g., different vertebrae and/or different portions of one or more vertebrae). For example, an orthopedic system can include a plurality of pedicle screws disposed along the length of a patient's spine, which may include an identical (or substantially identical) set of pedicle screws anchored on each side of the spine (e.g., as shown for one side of a patient's spine in FIGS. 9 and 10).

As shown in FIG. 2, the cylindrical shaft 210 and the tulip 222 may be physically coupled together with the cylindrical shaft 210 secured to at least a portion of the tulip 222. For example, the tulip 222 may be configured with a helical inclined plane 228, or female threads, formed in the conduit 224 of the tulip 222 and configured to engage and mate with a corresponding plurality of threads, or a helical inclined plane, that wrap around at least a portion of the cylindrical shaft 210. Stated differently, the tulip 222 and the cylindrical shaft 210 are configured to physically connect by mating and engaging corresponding sets of threads and/or corresponding helical inclined planes formed in each of the conduit 224 of the tulip 222 and a portion (e.g., a first end portion) of the cylindrical shaft 210.

In some embodiments, the cylindrical shaft 210 may engage the tulip 222 by placing the end of the shaft 210 with the helical inclined plane (e.g., the threaded end, opposite the eyelet 216) at an opening of the conduit 224 of the tulip 222. The cylindrical shaft 210 may be rotated by a user (e.g., by hand) and/or using one or more tools that may grasp a portion of the orthopedic screw 218 (e.g., the eyelet 216) and may enable a user (e.g., a physician) to engage the cylindrical shaft 210 and the tulip 222 (or the threads thereof) to a desired tightness or with a desired torque. Alternatively, or in addition, an eyelet may include an end portion (e.g., at the topmost portion of the eyelet 216), which is not shown in FIG. 2, and which may be configured to receive one or more tools used to manipulate and/or tighten a cylindrical shaft (e.g., cylindrical shaft 210) within the conduit of a tulip (e.g., the conduit 224 of the tulip 222). For example, in some embodiments, an eyelet may include one or more fastener heads to use in tightening a cylindrical shaft (e.g., shaft 210) to a tulip (e.g., tulip 222) including, for example: Phillips, hexagon drive, hexagon drive with hexalobular TX drive, Torx, security T, etc.

In some embodiments, the orthopedic screw 218 may engage and/or adjust a clamping mechanism of a tulip. The orthopedic screw 218 may be tightened to tighten the clamping mechanism for securing a rod in the channel of the tulip (e.g., the channel 226 of the tulip 222). The orthopedic screw 218 may be loosened to loosen the clamping mechanism. In other words, the orthopedic screw 218 may not directly engage a rod, but nevertheless may operate to secure a rod by adjusting or otherwise manipulating or activating an clamping mechanism.

The eyelet 216 can be configured to receive and secure a tether 240 at a first end 242 of the tether 240 (e.g., by receiving a portion of the tether 240, and/or a portion of the first end 242, therethrough). Stated differently, a portion of the tether 240 may be threaded through the eyelet 216, including, for example, the first end 242 of the tether 240. The first end of the tether 242 can be looped through the eyelet 216 and tied (e.g., to another portion of the tether 240), fastened (e.g., via one or more adhesives), or otherwise secured (e.g., via a knot of sufficient size that is tied in the first end of the tether 242) to (at) the eyelet 216. The eyelet 216, therefore, may secure the first end 242 of the tether 240 at a first point on the spine, or at a first location relative to the spine, which may correspond to the location of the eyelet 216. As described previously, the tether 240 may further include a second end (not shown) that can be similarly secured at a second point relative to the spine, or at a second location relative to the spine (e.g., at a portion of the spinous process or at another eyelet disposed at a distance from the eyelet 216).

As described herein, the tether 240 may be formed from a material suitable for use in an orthopedic procedure. For example, the tether 240 may be formed from MERSILENE® tape, a polyester fiber, and/or any material suitable for use as a tether in an orthopedic procedure. As described with reference to the tethers 140A and 140B shown in FIG. 1, the tether 240 may be positioned, sized, and/or otherwise configured to prevent, inhibit, and/or substantially reduce, an amount of movement (e.g., a forward movement) of a portion of the spine to which the system 200 is secured. For example, the tether 240 and the hardware to which the tether 240 is secured (e.g., the position of the eyelet 216 and/or the position of the pedicle screw 220 to which the cylindrical shaft is coupled), may be configured to control the position of one or more portions of the spine of a patient.

Figure 3:
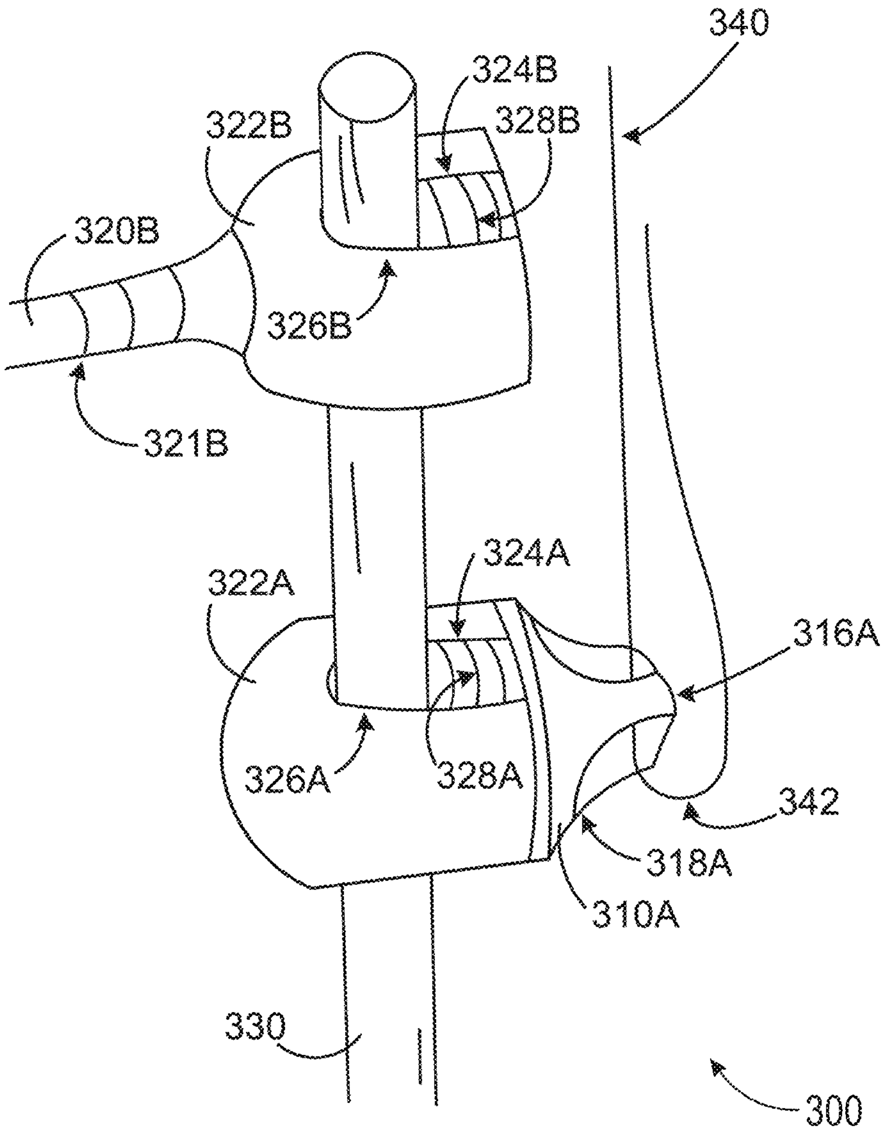
FIG. 3 is an orthopedic system for treating a spinal condition, according to one embodiment of the present disclosure.

FIG. 3 is an orthopedic system 300 for treating a spinal condition, according to one embodiment of the present disclosure. The orthopedic system 300 can include a first tulip 322A, an orthopedic screw 318A, which can include a cylindrical shaft 310A and an eyelet 316A, a rod 330, a tether 340, a pedicle screw 320B, and a second tulip 322B. In some embodiments, the rod 330, or a portion thereof, can be secured between the first tulip 322A and the cylindrical shaft 310A of the orthopedic screw 318A. The first tulip 322A may be a universal tulip configured to engage the rod 330 which may have been installed at the spine during a current spinal treatment procedure or during a previous spinal treatment procedure. Additionally, in some embodiments, the second tulip 322A can be configured to receive a portion of the rod 330 that is disposed a distance from the portion of the rod 330 secured by the first tulip 322 and the cylindrical shaft 310A of the orthopedic screw 318A.

As described above, the orthopedic screw 318, and specifically the cylindrical shaft 310A, is configured to couple to the first tulip 322A and secure the cylindrical shaft 310A to at least a portion of the first tulip 322A (e.g., the conduit 324A of the first tulip 322A). For example, the first tulip 322A may be configured with a helical inclined plane 328A (e.g., female threads) that is formed in the conduit 324A of the first tulip 322A, and which may be configured to engage and mate with a corresponding helical inclined plane (e.g., male threads), that wraps around at least a portion of the cylindrical shaft 310A of the orthopedic screw 318A. Stated differently, the first tulip 322A and the cylindrical shaft 310A of the orthopedic screw 318A are configured to physically connect by mating and engaging corresponding sets of threads formed in each of the conduit 324A of the first tulip 322A (e.g., female threads) and the cylindrical shaft 310A of the orthopedic screw 318A (e.g., male threads).

In some embodiments, the orthopedic screw 318A, specifically the cylindrical shaft 310A, may engage the first tulip 322A by placing the end of the shaft 310A with the helical inclined plane (e.g., the threaded end of the orthopedic screw 318A disposed opposite the eyelet 316A) at an opening of the conduit 324A of the first tulip 322A. The cylindrical shaft 310A may be rotated by a user (e.g., by hand) and/or using one or more tools that may engage a portion of the orthopedic screw 318A (e.g., by gripping the eyelet 316A and/or any portion thereof) and may enable a user (e.g., a physician) to engage the cylindrical shaft 310A and the first tulip 322A (or the threads thereof) to a desired tightness and/or with a desired torque. Accordingly, and as described above, the cylindrical shaft 310A and the first tulip 322A may be physically coupled together with the cylindrical shaft 310A secured to at least a portion of the first tulip 322A.

The eyelet 316A of the orthopedic screw 318A can be configured to receive and secure a tether 340 at a first end 342 of the tether 340 (e.g., by receiving a portion of the tether 340 and/or the first end 342, which may be looped through the eyelet 316A). The eyelet 316A may secure the first end 342 of the tether 340 at a first point on the spine (not shown). Stated differently, a portion of the tether 340 may be threaded through the eyelet 316A, including, for example, the first end 342 of the tether 340. To secure the tether 340 to the eyelet 316A, the first end of the tether 342 can be looped through the eyelet 316A and tied (e.g., to another portion of the tether 340), fastened (e.g., via one or more adhesives), or otherwise secured (e.g., via a knot tied in the tether 340 and of sufficient size to prevent the end of the tether 342 from exiting the eyelet 316A) to the eyelet 316A. The eyelet 316A, therefore, may secure the first end 342 of the tether 340 at a first point on the spine (not shown), which may correspond to the location of the eyelet 316A. As described previously, the tether 340 may further include a second end (not shown) that can be similarly secured at (e.g., threaded through) a second point relative to the spine (e.g., threaded through a hole formed in a portion of the spinous process of the spine, as shown in FIG. 1, or at a different eyelet that is disposed at a particular distance from the eyelet 316A).

The orthopedic system 300 can further include a second tulip 322B, which is configured to at least receive a portion of the rod 330, and a pedicle screw 320. Similar to the first tulip 322A, the second tulip 322B may be physically coupled to, and/or formed as part of, a pedicle screw 320B that is configured to be secured to, and/or inserted at, a vertebrae of the spine of a patient at a distance from the location of the pedicle screw (not shown) of the first tulip 322A.

The second tulip 322B is coupled to, and/or physically connected to, at least a portion of the pedicle screw 320B (e.g., an end portion of the shaft of the pedicle screw 320B), as shown in FIG. 3. The pedicle screw 320B can include a plurality of threads 321B, or a helical inclined plane, that wrap around a shaft of the pedicle screw 320B and are configured to secure the pedicle screw 320B to a portion of a patient's spine. The orthopedic system 300 can be secured to the spine via the pedicle screw 320B and may further be secured to the spine via one or more additional pedicle screws that are analogous to the pedicle screw 320B shown in, and described with reference to, FIG. 3.

As described above with reference to the first tulip 322A and the cylindrical shaft 310A, the second tulip 322B may be configured to retain and/or secure, potentially along with one or more additional components (e.g., one or more additional tulips and/or other components), the rod 330 or a portion thereof. As shown in FIG. 3, the second tulip 322B may secure, or at least receive (e.g., come in physical contact with), a portion of the rod 330 that is disposed within a channel 326B of the second tulip 322B. As can be seen in FIG. 3, the portion of the rod 330 in contact with the second tulip 322B may be a portion of the rod 330 that is disposed a distance from the portion of the rod 330 that is secured by, or in contact with, the first tulip 322A (e.g., the channel 326A of the first tulip 322A) and the cylindrical shaft 310A. The second tulip 322B may be fastened to the rod 330, or a portion thereof, without a cylindrical shaft coupled to the second tulip 322B. Instead, the second tulip 322B may secure the rod 330 to the channel 326B of the second tulip 322B via a traditional set screw (not shown), which may not include an eyelet and which has one or more threads that are configured to engage and mate with the threads 328B of the second tulip 322B (e.g., with a plurality of threads that are configured to be similar to the threads and/or helical inclined plane of a cylindrical shaft).

Figure 4:
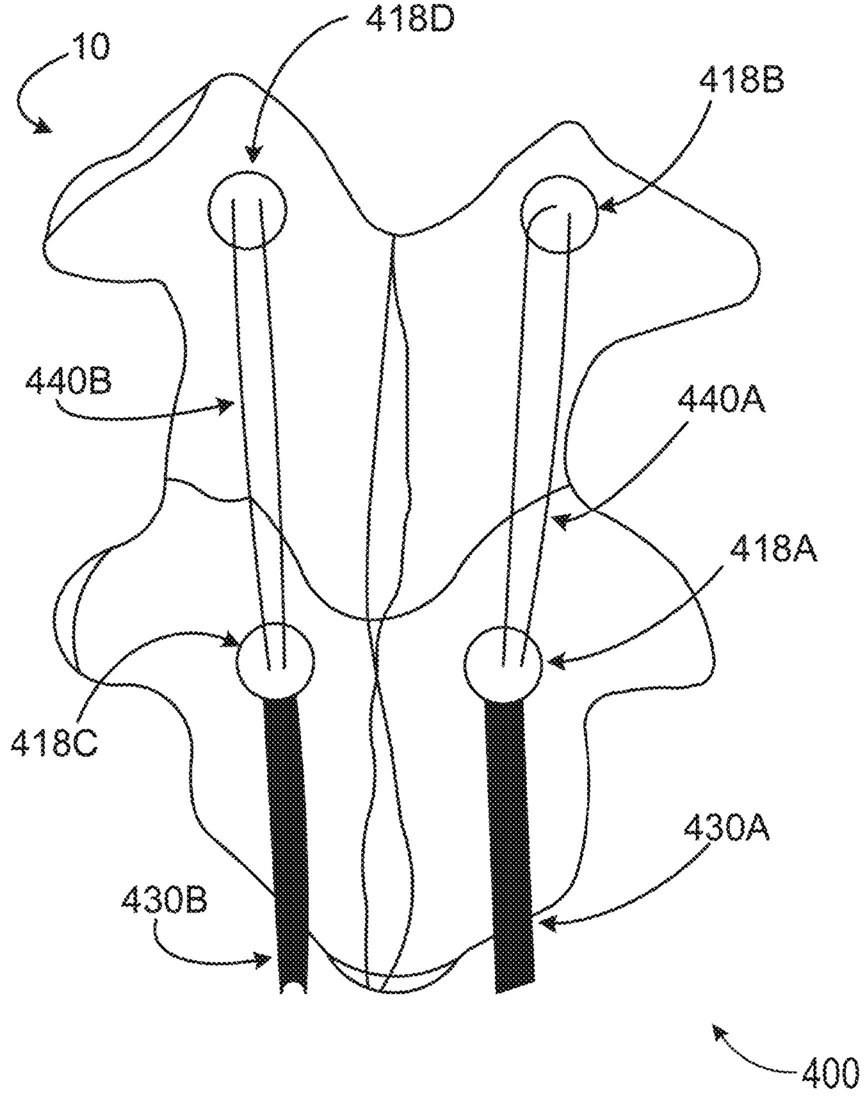
FIG. 4 is a rear view of the anatomy and placement of an orthopedic system for treating a spinal condition, according to one embodiment of the present disclosure.

FIG. 4 is a rear view of the anatomy of a spine 10 of a patient and placement of an orthopedic system 400 for treating a spinal condition, according to one embodiment of the present disclosure. The portion of the orthopedic system 400 that is shown in FIG. 4 includes a first orthopedic screw 418A, a first tether 440A, a second orthopedic screw 418B, a third orthopedic screw 418C, a second tether 440B, a fourth orthopedic screw 418D, a first rod 430A, and a second rod, 430B. As described above, the orthopedic system 400 is shown from the rear of a patient, at a view of the patient's spine 10 from behind.

The first tether 440A is shown with one end secured at the first orthopedic screw 418A, such as by threading the first tether 440A, or a portion thereof, through an eyelet of the first orthopedic screw 418A. As is shown in FIG. 4, the first orthopedic screw 418A is disposed proximate to the first rod 430A and, as described above, the first orthopedic screw 418A may be coupled toa pedicle screw that is physically coupled to the spine. The pedicle screw to which the first orthopedic screw 418A is coupled can include a tulip that is configured to receive, and to be secured to, the rod 430A. For example, the tulip may be secured to the rod 430A by physically coupling with the orthopedic screw 418A, or a portion thereof (e.g., a cylindrical shaft of the orthopedic screw 418A), with the rod 430A disposed between the tulip and the first orthopedic screw.

Similarly, in some embodiments, the first tether 440A may be further coupled to, and/or secured at, an eyelet of the second orthopedic screw 418B. As shown in FIG. 4, the first tether 440A may be disposed along a portion of the length of the spinous process of the spine 10, between the first orthopedic screw 418A and the second orthopedic screw 418B, which can be coupled to the spine 10 (e.g., via a pedicle screw and corresponding tulip) at a distance above the first orthopedic screw 418A. A portion of the first tether 440A that is threaded through an eyelet (not shown) of the first orthopedic screw 418A may couple to an eyelet (not shown) of the second orthopedic screw 418B.

The second tether 440B is oriented to be approximately parallel to the first tether 430A and can be disposed a lateral distance from (e.g., to the left of) the first tether 440A. The second tether 430B can be configured with one end disposed through an eyelet of the third orthopedic screw 418C, which can be physically secured to the second rod 430B or a portion thereof. In some embodiments, the second rod 430B may be physically engage by a third orthopedic screw 418C at a tulip of a pedicle screw. Additionally, the second tether 440B, or a portion thereof, may be coupled to, or secured at, an eyelet (not shown) of the third orthopedic screw 418C, as similarly described previously for the orthopedic screws, eyelets and tethers of the embodiments described above with reference to FIGS. 1-3.

As shown in FIG. 4, the second tether 440B may be disposed along a portion of the length of the spinous process of the spine 10, approximately parallel to the first tether 430A, the second tether 430B configured with one end secured at the third orthopedic screw 418C and another end secured at the fourth orthopedic screw 418D, which is disposed a vertical distance above the third orthopedic screw 418C. For example, a portion of the second tether 440B may be threaded through an eyelet of the third orthopedic screw 418C and another portion of the second tether 430B may be threaded through an eyelet of the fourth orthopedic screw 418D, similar to the orthopedic screws, eyelets, and tethers of one or more of the embodiments described above with reference to FIGS. 1-3.

Figure 5:
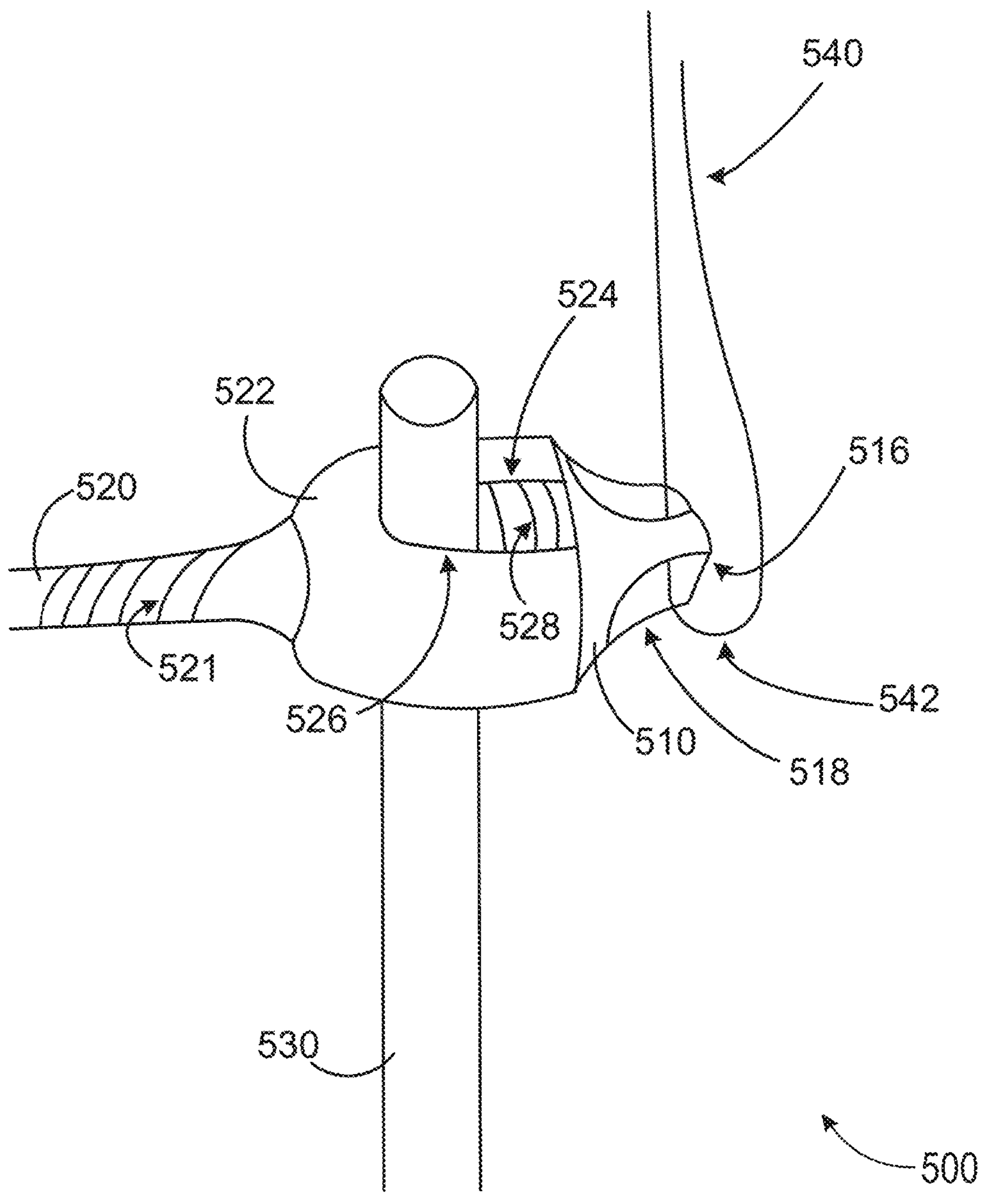
FIG. 5 is an orthopedic system for treating a spinal condition, according to one embodiment of the present disclosure.

FIG. 5 is an orthopedic system 500 for treating a spinal condition, according to one embodiment of the present disclosure. The orthopedic system 500 is configured to be secured to at least a portion of a spine (e.g., via one or more pedicle screws inserted into the spine of a patient) and can include a cylindrical shaft 510, including an eyelet 516, which is coupled to a tulip 522 of a pedicle screw 520, a rod 530, and a tether 540. As shown in FIG. 5, the tulip 522 is coupled to, and/or physically attached to, at least a portion of the pedicle screw 520 (e.g., an end portion of the shaft of the pedicle screw 520). The tulip 522 may be a universal tulip, which is configured to engage and/or secure to the rod 530 that may be installed (e.g., via pedicle screws) at the spine 10. Stated otherwise, the tulip 522 may be configured to couple with one or more different types of components, including, for example, components associated with one or more different manufacturers, products, techniques, and the like. The pedicle screw 520 can include a plurality of threads 521, or a helical inclined plane, that wrap around a shaft of the pedicle screw 520 and are configured to secure the pedicle screw 520 to a portion of a patient's spine (e.g., to secure the pedicle screw 520 at a location on the spine). The orthopedic system 500 can be secured to the spine via one or more pedicle screws (e.g., pedicle screw 520) attached to one or more corresponding tulips (e.g., the tulip 522), which can be configured to physically engage and mate with (e.g., couple and/or fasten to), one or more corresponding orthopedic screws (e.g., physically couple with the cylindrical shaft 510 of the orthopedic screw 518).

As described previously, orthopedic screw 518, specifically the cylindrical shaft 510, and the tulip 522 may be configured to retain and/or secure at least a portion of the rod 530. For example, the tulip 522 may be configured with a channel 526 that is configured (e.g., sized, shaped, etc.) to physically receive and/or couple with the rod 530 or portion thereof. Additionally, the cylindrical shaft 510 of the orthopedic screw 518 may be configured to couple with the tulip 522, including at a conduit 524 formed by the tulip 522 and configured to receive the cylindrical shaft 510. The cylindrical shaft 510 may be configured to engage and/or physically contact a portion of the rod 530 disposed within the channel 526 of the tulip 522 (e.g., the cylindrical shaft 510 configured to abut the rod 530, and/or a fastener disposed between the rod 530 and the cylindrical shaft 510, to secure the rod 530 against the channel 526 of the tulip 522). Accordingly, the tulip 522 and the orthopedic screw 518 (e.g., the cylindrical shaft 510) may be configured to physically couple in a way that can secure the rod 530, or a portion thereof, to the tulip 522 as part of the orthopedic system 500 (e.g., to provide rigid physical support to one or more portions of the spine of a patient).

Figure 8:
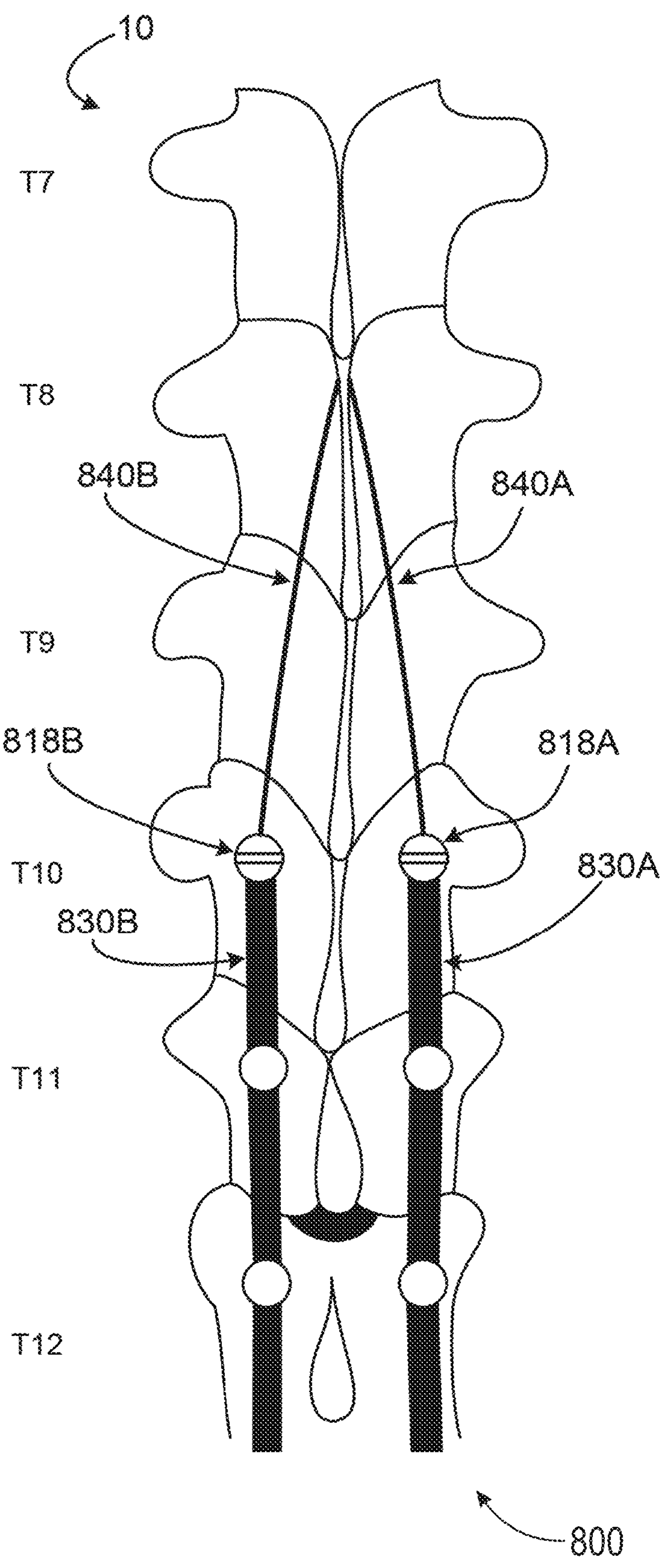
FIG. 8 is a rear view of the anatomy and placement of an orthopedic system for treating a spinal condition, according to one embodiment of the present disclosure.
Figure 9:
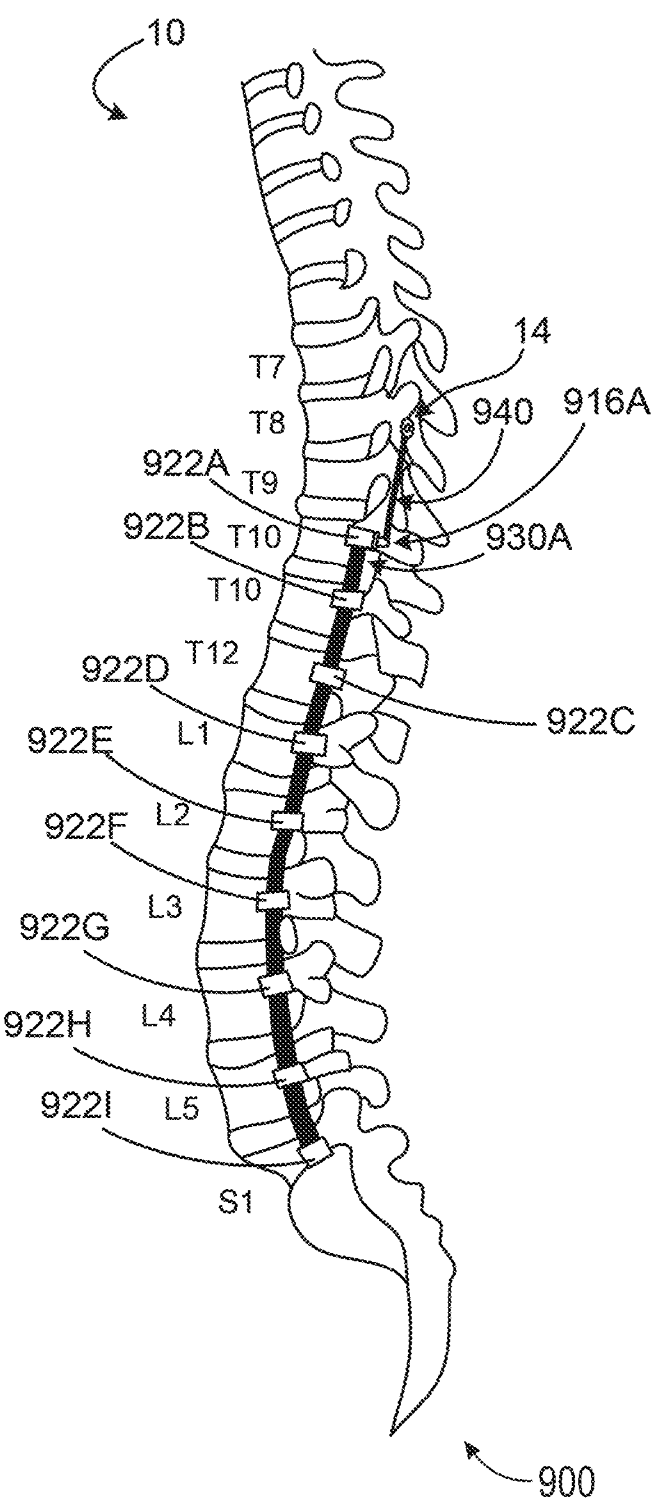
FIG. 9 is a lateral view of the anatomy and placement of an orthopedic system for treating a spinal condition, according to one embodiment of the present disclosure.
Figure 10:
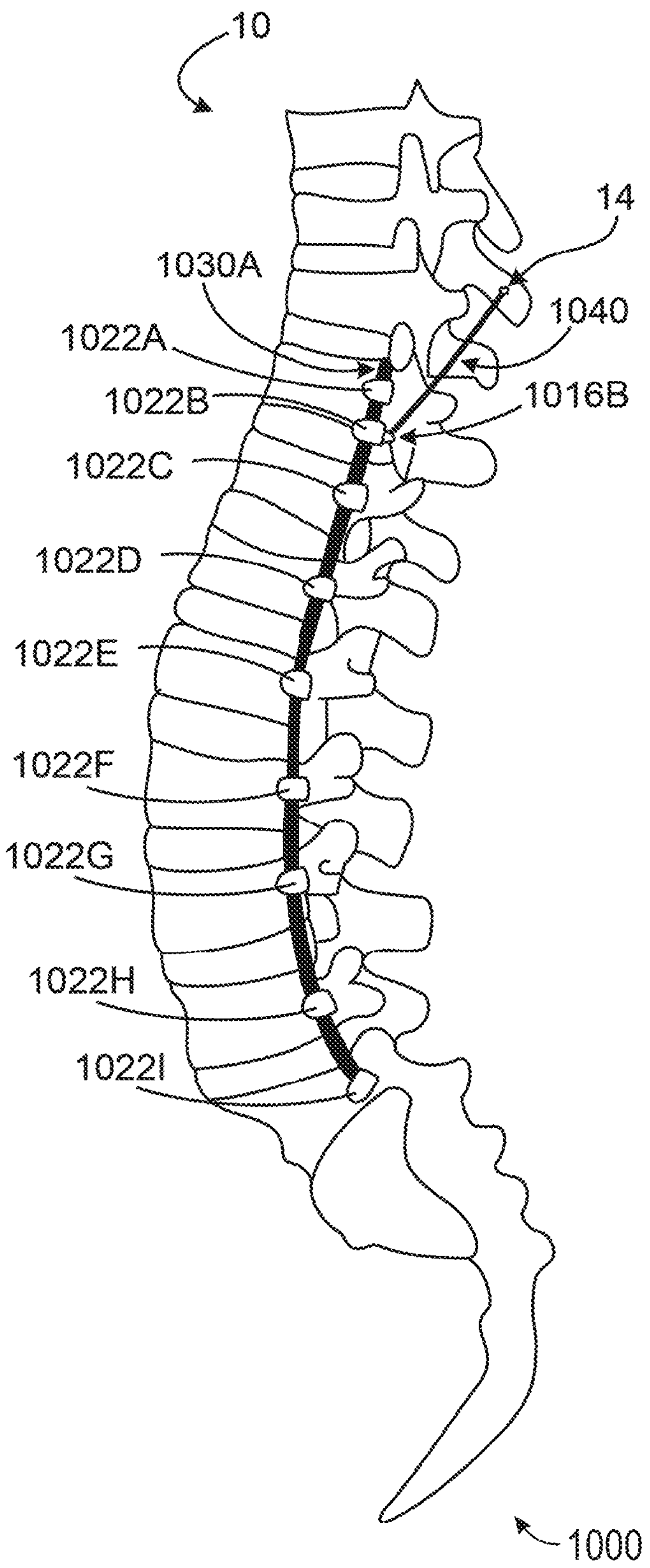
FIG. 10 is a lateral view of the anatomy and placement of an orthopedic system for treating a spinal condition, according to one embodiment of the present disclosure.

The system 500 is configured to be secured to at least a portion of a patient's spine. For example, the pedicle screw 520, or at least a portion thereof, is configured to insertion into a patient's spine. More specifically, the pedicle screw 520 and the plurality of threads that wrap around a shaft of the pedicle screw 520 are configured to be anchored in, and/or fastened to, a portion of a patient's spine and/or one or more vertebrae. Some embodiments of the orthopedic systems disclosed herein can include a plurality of pedicle screws (e.g., similar to the pedicle screw 520) that can each be anchored at and/or secured to, a portion of a patient's spine (e.g., at one or more different vertebrae and/or different portions of one or more vertebrae). For example, an orthopedic system can include a plurality of pedicle screws disposed along the length of a patient's spine (e.g., as shown in FIGS. 9 and 10), which may include an identical (or substantially identical) set of pedicle screws anchored on each side of the spine (e.g., as shown in FIG. 8).

As shown in FIG. 5, the cylindrical shaft 510 of the orthopedic screw 518 can be physically coupled with, and/or attached to, the tulip 522 of the pedicle screw 520 with the cylindrical shaft 510 physically secured to at least a portion of the tulip 522. For example, the tulip 522 may be configured with a helical inclined plane 528 (e.g., a plurality of female threads) formed in the conduit 524 of the tulip 522, which can be configured to engage and mate with a corresponding helical inclined plane (e.g., male threads) that wraps around at least a portion of the cylindrical shaft 510 of the orthopedic screw 518. Stated differently, the tulip 522 and the cylindrical shaft 510 are configured to physically connect by mating and engaging corresponding sets of threads and/or corresponding helical inclined planes formed in each of the conduit 524 of the tulip 522 and a portion (e.g., a first end portion) of the cylindrical shaft 510.

In some embodiments, the cylindrical shaft 510 may engage the tulip 522 by placing the end of the shaft 510 with the helical inclined plane (e.g., the threaded end, opposite the eyelet 516) at an opening of the conduit 524 of the tulip 522. The cylindrical shaft 510 may be rotated by a user (e.g., by hand) and/or using one or more tools that may grasp a portion of the orthopedic screw 518 (e.g., the eyelet 516) and may enable a user (e.g., a physician) to engage the cylindrical shaft 510 with the tulip 522 (or the female threads thereof) to a desired tightness or with a desired torque. Alternatively, or in addition, the eyelet 516 of the orthopedic screw 518 may include an end portion (e.g., at the topmost portion of the eyelet 516), which is not shown in FIG. 5, and which may be configured to receive one or more tools used to manipulate and/or tighten a cylindrical shaft (e.g., cylindrical shaft 510) within the conduit of a tulip (e.g., the conduit 524 of the tulip 522). Additionally, in some embodiments, the eyelet 516 may be disposed at a head of the orthopedic screw 518, the head located at a second end of the cylindrical shaft 510 opposite a first end of the cylindrical shaft 510. In some embodiments, the helical inclined plane (e.g., the plurality of male threads) can be disposed at the first end of the shaft 510, the first end configured to abut and physically secure the rod 530 against the tulip 522.

The eyelet 516 of the orthopedic screw 518 can be configured to receive and secure a tether 540 at a first end 542 of the tether 540 (e.g., by receiving a portion of the tether 540, and/or a portion of the first end 542, therethrough). Stated differently, a portion of the tether 540, such as the first end 542, may be threaded through the eyelet 516 to secure the tether 540 to the eyelet 516, the orthopedic screw 518, or the part of the spine to which the orthopedic screw 518 is fastened (e.g., via the pedicle screw 520). The first end of the tether 542 can be looped through the eyelet 516 and tied (e.g., to another portion of the tether 540), fastened (e.g., via one or more adhesives), or otherwise secured (e.g., via a knot of sufficient size that is tied in the first end of the tether 542) to (at) the eyelet 516. The eyelet 516, therefore, may secure the first end 542 of the tether 540 to the orthopedic screw 518 and/or at a first point on the spine, which may correspond to the location of the eyelet 516, the orthopedic screw 518, and/or the pedicle screw 520. As described previously, the tether 540 may further include a second end (not shown) that can be similarly secured at a second point relative to the spine (e.g., at a portion of the spinous process or at another eyelet that is located a distance from the eyelet 516, which can be a different portion of the spine and/or vertebrae of the patient).

Figures 6A, 6B:
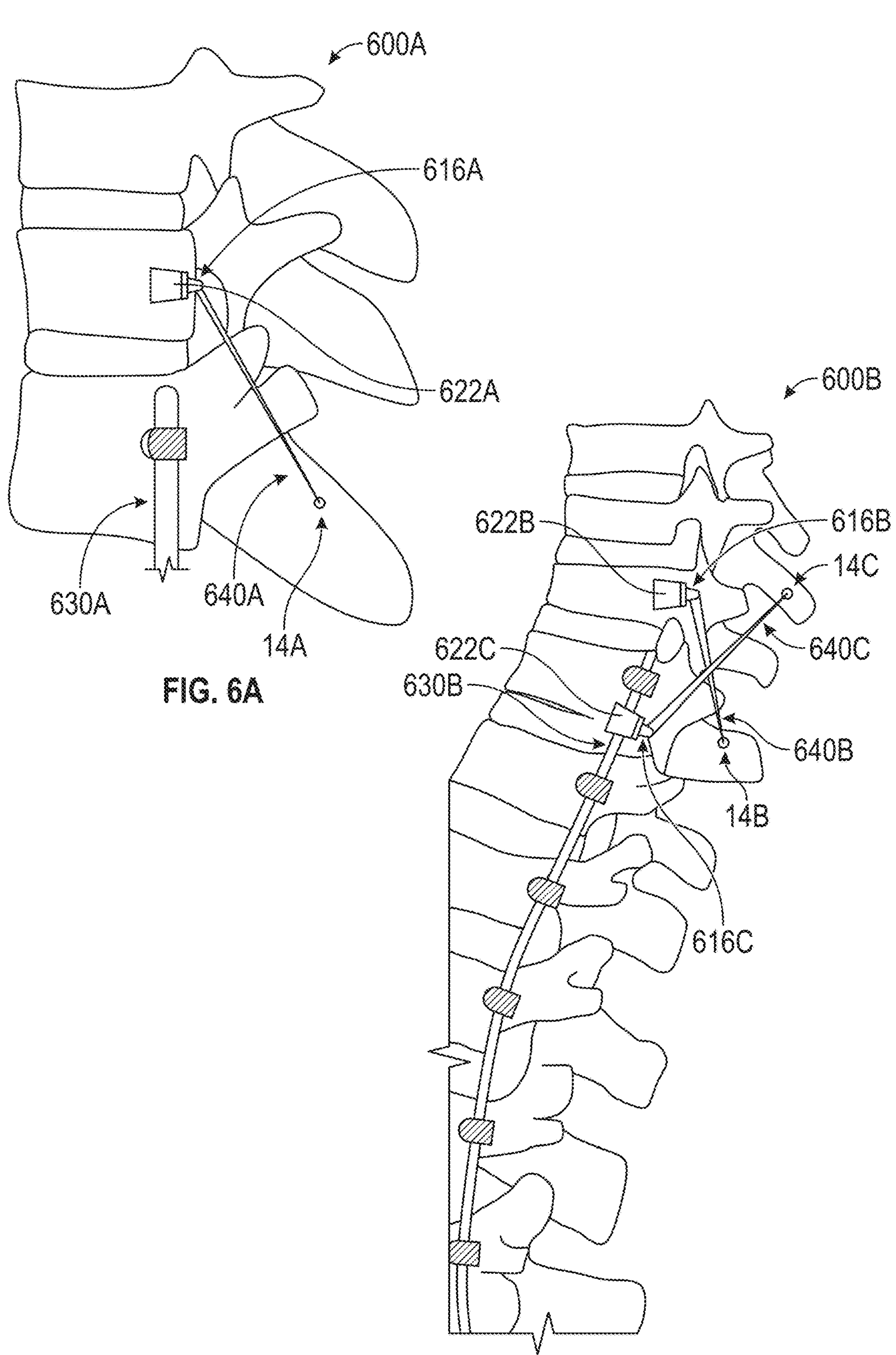
FIG. 6A is a lateral view of the anatomy and placement of an orthopedic system for treating a spinal condition, according to one embodiment of the present disclosure.
FIG. 6B is a lateral view of the anatomy and placement of an orthopedic system for treating a spinal condition, according to one embodiment of the present disclosure.

FIG. 6A is a lateral view of the anatomy of a patient and of the placement of an orthopedic system 600A for treating a spinal condition, according to one embodiment of the present disclosure. The system 600A includes a tulip 622A, an eyelet 616A of an orthopedic screw, a tether 640, and a rod 630A. The tulip 622A, as described above with reference to other embodiments, may be physically attached to a pedicle screw configured to be fastened to a portion of the spine at the location of the tulip 622A (e.g., secured to the spine by a pedicle screw anchored in the portion of the spine at, or near, the location of the tulip 622A shown in FIG. 6A). The eyelet 616A may be formed by, or be part of, an orthopedic screw that further includes a cylindrical shaft, which is configured to be coupled with, or screwed into, a conduit of the tulip 622A. In another embodiment, the eyelet 616A may be formed by, or be part of, an orthopedic screw that further includes a cylindrical shaft, which is configured to be inserted into the pedicle of a vertebra of the spine. Further The tether 640A can be connected to the eyelet 616A of the orthopedic screw at a first end (e.g., the end of the tether 640A proximate to the eyelet 616A) and may be fastened to, or disposed through, a portion of the patient's spine 10 at a second end (e.g., the end of the tether 640A opposite the end at the eyelet 616A). For example, the tether 640A may be fastened to a portion of the spinous process of the spine and/or it may be secured to a hole 14A in the spinous process, as shown in FIG. 6A. The first end of the tether 640A, the tulip 622A, and the eyelet 616A may be disposed at or proximate to a portion of the spine that is above the rod 630A, or at a non-fused portion of the spine. As described above, the rod 630A may be physically connected (e.g., via one or more pedicle screws) to a portion of the spine 10 (e.g., a fused portion of the spine) and, as shown in FIG. 6A, the rod 630A may be disposed below the eyelet 616A.

In some embodiments, the positioning of the tether 640, the eyelet 616A of the orthopedic screw, and the rod 630 can be configured to reduce, inhibit, and/or resist an amount of movement of a portion of the spine above the rod 630A. Stated differently, the portion of the spine 10 coupled, via the pedicle screw and the tulip 622A, to the orthopedic screw of the eyelet 616A can be at least partially restrained and/or secured by the tether 640A against forward movement relative to the rod 630A. Stated otherwise, the tether 640A may apply a force to the portion of the spine coupled to the first end of the tether 640A, which is a non-fused portion of the spine disposed above the portion of the spine to which the rod 630A is attached (e.g., via pedicle screws), or above a fused portion of the spine. In some embodiments, the first end of the tether 640A, the tulip 622A, and the eyelet 616A may be disposed at or proximate to an upper instrumented vertebrae (UIV) that is +1 or +2, meaning 1 or 2 levels above the last instrumented level in a fusion construct (or fused portion of the spine).

FIG. 6B is a lateral view of the anatomy of a patient and of the placement of an orthopedic system 600B for treating a spinal condition, according to one embodiment of the present disclosure. The system 600B includes a first tulip 622B of a pedicle screw, a first eyelet 616B of an orthopedic screw, a first tether 640B, a second tulip 622C, a second eyelet 616C, a second tether 640C, and a rod 630B.

The first tulip 622B, similar to tulips of embodiments described above, may be physically attached and/or fastened to a pedicle screw that is inserted into a portion of the spine located at the position of the first tulip 622B shown in FIG. 6B (e.g., via a pedicle screw attached to the first tulip 622B, which is anchored in the portion of the spine at the location of the first tulip 622B). The first eyelet 616B may be formed by, or be part of, an orthopedic screw. The orthopedic screw of the first eyelet 616B may further include a cylindrical shaft that is configured to be coupled with, or screwed into, a conduit of the first tulip 622B. The first tether 640B can be connected to, or secured at, the first eyelet 616B of the orthopedic screw. In some embodiments, the first tether 640B can be secured to the first eyelet 616B at a first end (e.g., the end of the first tether 640B proximate to the first eyelet 616B) and a second end of the first tether 640B may be fastened to, threaded through, and/or secured at, a portion of the patient's spine disposed at a distance from the first eyelet 616B. For example, the second end of the first tether 640B may be fastened to, or secured at, a portion of the spinous process of the spine, or a hole 14B that is formed in the spinous process of the spine 10, as shown in FIG. 6B. The first end of the first tether 640B, the first tulip 622B, and the first eyelet 616B may be disposed at or proximate to a portion of the spine that is above the rod 630B. In some embodiments, the first end of the first tether 640B, the tulip 622B, and the eyelet 616B may be disposed at or proximate to an upper instrumented vertebrae (UIV) that is +1 or +2, meaning 1 or 2 levels above the last instrumented level in a fusion construct (or fused portion of the spine). As described above, the rod 630B, and one or more of the tulips 622, may be physically connected (e.g., via one or more pedicle screws) to the spine. Further, as also shown in FIG. 6B, the rod 630B can be disposed at a location that is below the orthopedic screw with the first eyelet 616B.

The second tulip 622C, similar tulips of other embodiments disclosed herein, may be physically attached to a pedicle screw that is fastened to a portion of the spine at the location of the second tulip 622C (e.g., anchored, via a pedicle screw, in the portion of the spine and/or vertebrae proximate to the second tulip 622C). The second eyelet 616C may be formed by, or be part of, an orthopedic screw (e.g., a second orthopedic screw), which may further include a cylindrical shaft (e.g., a second cylindrical shaft) that is configured to be coupled with, or screwed into, a conduit of the second tulip 622C. Further, the second tether 640C can be connected to the second eyelet 616C at a first end of the second tether 640C (e.g., the end of the second tether 640C that is proximate to the second eyelet 616C) and a second end of the second tether 640C may be fastened to, or threaded through, and/or secured at a portion of the patient's spine. For example, the second tether 640C may be fastened to a portion of the spinous process and/or it may be secured to a second hole 14C in the spinous process, as shown in FIG. 6B. The first end of the second tether 640C, the second tulip 622C, and the second eyelet 616C may be disposed at, or be proximate to, a portion of the spine that is disposed above the rod 630B or at least a portion thereof (e.g., above a majority portion of the rod 630B, the second tulip 622C and the second eyelet 616C both disposed below the first tulip 622B and the first eyelet 616B). As described in the previous paragraph, the rod 630B may be physically connected (e.g., via one or more pedicle screws physically attached to one or more corresponding tulips) to a portion of the spine and, as shown in FIG. 6B, the rod 630B may be disposed along, and fastened to, a plurality of different vertebrae of the spine (e.g., the rod 630B may extend along a portion of the spine that is disposed below the second eyelet 616C).

In some embodiments, the first and second tethers 640B 640C, the first and second tulips 622B 622C, and the first and second eyelets 616B 616C can be configured (e.g., positioned, sized, tightened, oriented, and/or the like) to reduce, inhibit, and/or resist an amount of movement of a portion of the spine above the rod 630B and/or a portion thereof. Stated differently, the portion of the spine coupled, via the first and second tethers 640B 640C, to the first and second eyelets 616B 616C may be at least partially restrained and/or secured by the first and second tethers 640B 640C against one or more types of movement (e.g., in a forward direction) relative to the rod 630B.

Figure 7:
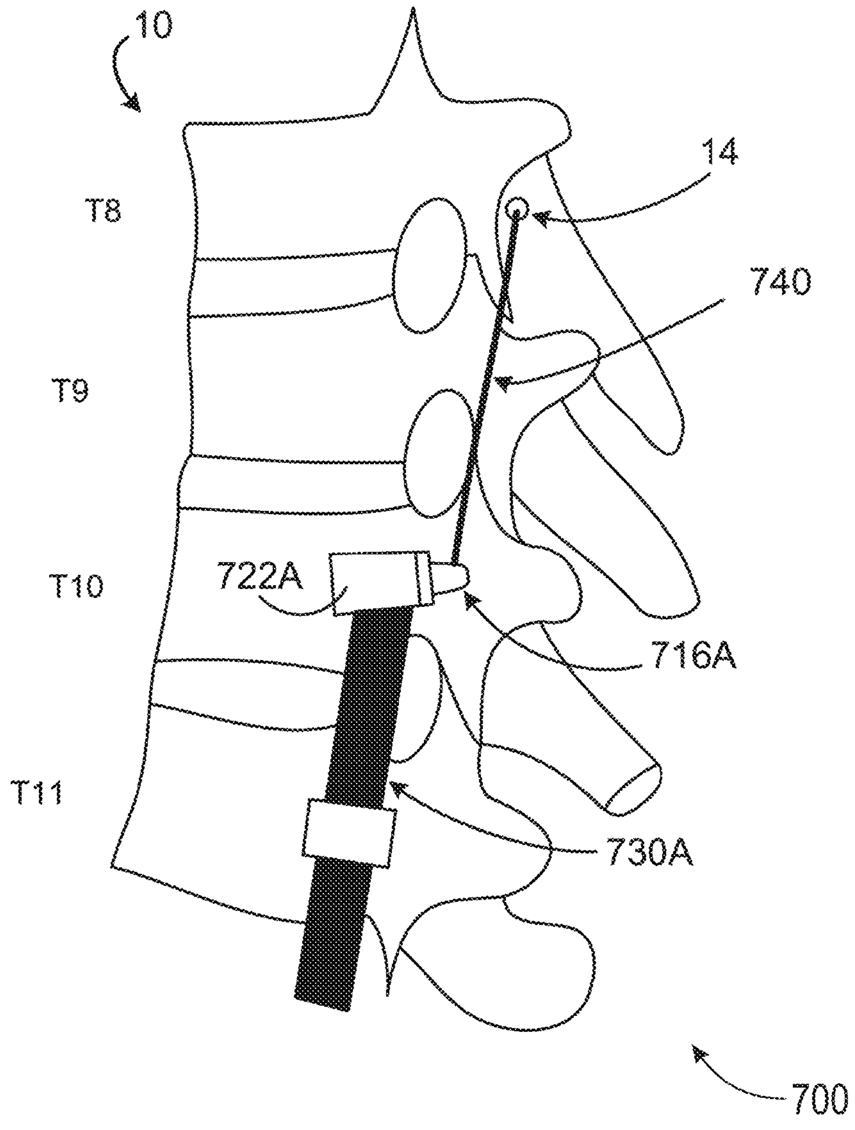
FIG. 7 is a lateral view of the anatomy and placement of an orthopedic system for treating a spinal condition, according to one embodiment of the present disclosure.

FIG. 7 is a lateral view of the anatomy and placement of an orthopedic system 700 for treating a spinal condition, according to one embodiment of the present disclosure. The system 700 is shown with a lateral view of a patient's spine 10, including a portion of the thoracic spine or vertebrae T8, T9, T10, and T11. The system 700 can include an eyelet 716A, a first tulip 722A, a rod 730A, and a tether 740. The tulip 722A can be fastened to, or formed from, a pedicle screw (not shown) that is coupled to, and/or anchored in, the T10 vertebrae. Similar to the eyelets and tulips described above, the eyelet 716A is coupled and/or fastened to the tulip 722A. For example, the eyelet 716 may be part of a cylindrical shaft (e.g., a set screw) that is screwed into (e.g., engaged and/or mated with) a threaded conduit formed in the tulip 722A.

The eyelet 716A can receive, and/or secure, the tether 740 including, more specifically, a first end of the tether 740, which may be threaded through the eyelet 716A to secure the tether 740 to the eyelet 716A and, as a result, to the tulip 722A and T10 vertebrae to which the tulip is fastened (e.g., via the pedicle screw, which is not shown in FIG. 7). Again similar to the tulips described above, the tulip 722A is configured to receive and secure the rod 730A and/or a portion thereof; including, for example, by receiving a portion of the rod 730 within a channel of the tulip 722A with an end or end portion of the set screw from which the eyelet 716A is formed likewise coming in physical contact with, and/or abutting against, the rod 730 to physically secure it between the eyelet 716A (e.g., the set screw and/or cylindrical shaft from which the eyelet 716A is formed) and the tulip 722A.

As also shown in FIG. 7, the tether 740 may also be fastened, at a second end, to a portion of the spinous process of the spine 10. More specifically, the tether 740 may be fastened to the spinous process proximate to the T8 vertebrae and at an end, or end portion, of the tether 740 opposite the end of the tether 740 that is coupled to the eyelet 716A.

FIG. 8 is a rear view of the anatomy and placement of an orthopedic system 800 for treating a spinal condition, according to one embodiment of the present disclosure. The system 800 is shown with a rear view of a patient's spine 10, including a portion of the thoracic spine or vertebrae T7, T8, T9, T10, T11, and T12. The system 800 can include a first orthopedic screw 818A, a first rod 830A, a first tether 840A, a second orthopedic screw 818B, a second rod 830B, and a second tether 840B.

Similar to the system 700 shown in FIG. 7, the first orthopedic screw 818A can be fastened to, a tulip, which is physically attached to a pedicle screw (not shown) coupled to, and/or anchored in, the T10 vertebrae. Similar to the orthopedic screws described above, the first orthopedic screw 818A can include, and/or be coupled to a first eyelet (not shown). For example, the first orthopedic screw 818A can include a first eyelet and a cylindrical shaft (e.g., a set screw) that is configured to be screwed into (e.g., engaged and/or mated with) a threaded conduit formed in the first orthopedic screw 818A and/or a portion thereof. In some embodiments, the first eyelet of the first orthopedic screw 818A can be formed at a head of the cylindrical shaft of the first orthopedic screw 818A.

The first tether 840A can be fastened to, and/or threaded through, the eyelet of the first orthopedic screw 818A, with one end of the first tether 840A coupled to the eyelet of the first orthopedic screw 818A and an opposite end of the first tether 840A secured at, coupled to and/or fastened to a portion of the spinous process, including, for example, a hole in a portion of the spinous process located at, or proximate to, vertebrae T8 (e.g., with the first tether 840 threaded through and/or coupled to a middle portion of the spine 10, at T8, as shown in FIG. 8).

The first orthopedic screw 818A may further be configured to secure, along with a set screw or threaded portion of the cylindrical shaft and a corresponding tulip that is configured to be coupled with the first orthopedic screw 818A, the first rod 830A and/or a portion thereof. The first orthopedic screw 818A may be configured to physically abut the first rod 830A to secure the rod 830A in a channel formed by the tulip that is coupled to the first orthopedic screw 818A. Additionally, the first rod 830A may be secured to one or more additional portions of the spine 10 by one or more additional tulips, which can each be anchored into, and/or fastened to, one or more portions (e.g., vertebrae) of the spine 10 via a corresponding pedicle screw that is physically attached to the tulip.

The second orthopedic screw 818B can be fastened, via a tulip, to a corresponding pedicle screw (not shown) that is physically attached to the tulip and that is coupled to, and/or anchored in, the T10 vertebrae (e.g., positioned at a location that is laterally offset with respect to, and/or disposed at a lateral distance from, the location of the first orthopedic screw 818A. Similar to the orthopedic screws described above, the second orthopedic screw 818B can include a second eyelet (not shown). For example, the second orthopedic screw 818B can include a second eyelet and a cylindrical shaft (e.g., a set screw) that is screwed into (e.g., engaged and/or mated with) a threaded conduit that is formed in the tulip that is coupled to the second orthopedic screw 818B and/or a portion thereof.

The second tether 840B can be fastened to, and/or threaded through, the eyelet of the second orthopedic screw 818B, with one end of the second tether 840B coupled to, or secured at, the eyelet of the second orthopedic screw 818B and an opposite end of the second tether 840B coupled to and/or secured at, a hole in a portion of the spinous process, including, for example, a portion of the spinous process located at, or proximate to, vertebrae T8 (e.g., a portion of the second tether 840B threaded through and/or coupled with a middle portion of the spine 10, at vertebrae T8, as shown in FIG. 8).

The second orthopedic screw 818B (e.g., a cylindrical shaft of the second orthopedic screw 818B) may further be configured to secure, along with a tulip configured to couple with the second orthopedic screw 818B, the second rod 830B and/or a portion thereof. The second orthopedic screw 818B may be configured to physically abut, and secure, the second rod 830B in a channel formed by, or in, a tulip that is coupled with the second orthopedic screw 818B. And the set screw, or cylindrical shaft, of the second orthopedic screw 818B may likewise be configured to physically abut and thereby secure, the second rod 830B between the tulip (or a pedicle screw from which it is formed) and the second orthopedic screw 818B. Additionally, the second rod 830B may be secured to one or more additional portions of the spine 10 by one or more additional tulips, which may be anchored into, and/or fastened to, one or more vertebrae of the spine 10 via corresponding pedicle screws (e.g., shown in FIG. 8 below the second orthopedic screw 818B and coupled to the second rod 830B).

FIG. 9 is a lateral view of the anatomy and placement of an orthopedic system 900 for treating a spinal condition, according to one embodiment of the present disclosure. The system 900, which is shown positioned along a spine 10 of a patient, includes a first tulip 922A, a first eyelet 916A of an orthopedic screw coupled with the first tulip 922A, a tether 940, a rod 930A, and a plurality of additional tulips 922B, 922C, 922D, 922E, 922F, 922G, 922H, 922I (tulips 922A-922I may be referred to collectively herein as tulips and/or the tulips 922A-I). As shown in FIG. 9, the tether 940 can be coupled at one end to the eyelet 916A of the orthopedic screw coupled to the tulip 922A and at another end to a hole 14 in the spinous process. In the system 900 shown in FIG. 9, the hole 14 in the spinous process is located at a portion of the spine that is proximate to and/or disposed in the spinous process of the T8 vertebrae.

Similar to the embodiments described above, the orthopedic screw of the eyelet 916A, or a cylindrical shaft thereof, may be screwed into, and/or fastened to, the first tulip 922, which may in turn be fastened to the spine 10 via a corresponding pedicle screw that is anchored into, and/or inserted at, the T10 vertebrae of the spine 10. Additionally, the first tulip 922A and the eyelet 916A (e.g., a threaded portion of the orthopedic screw of the eyelet 916A) may be configured to secure the rod 930A, or a portion thereof, with the tulip 922A and the cylindrical shaft of the orthopedic screw for the eyelet 916A configured to physically abut, and thereby secure, the rod 930A and/or a portion thereof, at the location of the first tulip 922A or a portion of the spine proximate thereto. Likewise, each of the additional tulips 922B-I may be configured to secure corresponding portions of the rod 930A by physically abutting against, and thereby securing, the rod 930A between the tulips 922B-I and corresponding set screws, or other fastener(s) configured to couple with the tulips 922 and secure the rod 930A, that are coupled with, and/or screwed into, the tulips 922B-I (e.g., as described above with reference to the second tulip 322B shown in FIG. 3 and the corresponding set screw which is not shown in, but is described with reference to, FIG. 3).

FIG. 10 is a lateral view of the anatomy and placement of an orthopedic system 1000 for treating a spinal condition, according to one embodiment of the present disclosure.

The system 1000, which is shown positioned along a spine 10 of a patient, includes a first tulip 1022A, second tulip 1022B, a first eyelet 1016B of an orthopedic screw, a tether 1040, a rod 1030A, and a plurality of additional tulips 1022C, 1022D, 1022E, 1022F, 1022G, 1022H, 1022I (the tulips 1022A-1022I may be referred to collectively herein as tulips 1022). As shown in FIG. 10, the tether 1040 can be coupled at one end to the eyelet 1016B of the orthopedic screw and at another end to a hole 14 in the spinous process of the spine 10.

Similar to the embodiments described above, the orthopedic screw of the eyelet 1016B (e.g., a cylindrical shaft of the orthopedic screw, or a portion thereof) may be screwed into, coupled with, and/or fastened to, the second tulip 1022B, which may in turn be fastened to the spine 10 via a pedicle screw that is physically attached to the second tulip 1022B. The pedicle screw of the second tulip 1022B can be anchored into, and/or inserted at, the vertebrae of the spine 10 or the portion of the spine where the second tulip 1022B is shown. Additionally, the second tulip 1022B and the eyelet 1016B (e.g., a threaded portion of the orthopedic screw of the eyelet 1016B) may be configured to secure the rod 1030A, or a portion thereof, with each of the tulip 1022B and the cylindrical shaft of the orthopedic screw of the eyelet 1016B physically abutting, and thereby securing, the rod 1030A and/or a portion thereof at the location of, or within the channel for, the second tulip 1022B. Likewise, each of the additional tulips 1022A and 1022C-I may be configured to secure corresponding portions of the rod 1030A by physically abutting against, and thereby securing, the rod 1030A between the tulips 1022A 1022C-I and corresponding set screws coupled with, and/or screwed into, the tulips 1022A 1022C-I (e.g., as described above with reference to the second tulip 322B shown in FIG. 3 and the corresponding set screw which is not shown in, but is described with reference to, FIG. 3).

EXAMPLES

The following are example embodiments of the present disclosure.

Example 1. An orthopedic screw comprising: a cylindrical shaft to be received into a conduit of a tulip of a pedicle screw, which is to be inserted into a vertebra of a patient to be treated for a spinal condition, the tulip including a channel to receive and interface with a rod, wherein a first end of the cylindrical shaft is configured to engage the rod and apply compressive force to secure the rod within the tulip; a helical inclined plane wrapping around the cylindrical shaft and configured to engage and mate with a corresponding helical inclined plane of the conduit the tulip; a head at a second end of the cylindrical shaft, the head to be manipulated during tightening or loosening of the orthopedic screw to rotate the cylindrical shaft and helical inclined plane into the conduit of the tulip; an eyelet disposed at the head, the eyelet configured to receive (and secure) a tether therethrough, wherein the tether extends through the eyelet, a first end of the tether is to be secured at a first point on the spine of the patient that is displaced a first distance from a point of securement of the pedicle screw on the vertebrae of the patient, and a second end of the tether is to be secured at a second point on the spine of the patient that is displaced a second distance from the point of securement of the pedicle screw on the vertebrae of the patient, and wherein the eyelet exerts a force on the tether, which transfers the force to the first point on the spine and the second point on the spine to stabilize a portion of the spine to counter bending of the spine of the patient.

Example 2. The orthopedic screw of Example 1, wherein the eyelet is further configured to receive and secure a second tether disposed through the eyelet.

Example 3. The orthopedic screw of Example 2, wherein the second tether is disposed substantially parallel to the spine.

Example 4. The orthopedic screw of Example 2, wherein the eyelet is further configured to provide a specific angle of orientation to the first tether.

Example 5. The orthopedic screw of Example 4, wherein the eyelet is further configured to provide a specific angle of orientation to the second tether.

Example 6. The orthopedic screw of Example 5, wherein the specific angle provided to the first tether is based on the specific angle provided to the second tether.

Example 7. The orthopedic screw of Example 5, wherein the specific angle of orientation of the first tether is 45 degrees.

Example 8. The orthopedic screw of Example 2, wherein the second tether is secured to a receiving eyelet at a third point on the spine of the patient that is displaced a third distance from a point of securement of the pedicle screw on the vertebrae of the patient.

Example 9. The orthopedic screw of Example 1, wherein the first tether is secured to a hole in the spinous process.

Example 10. The orthopedic screw of Example 1, wherein the first tether is not secured to the spinous process.

Example 11. An orthopedic screw for use in spinal treatment procedures to secure a rod to a tulip of a pedicle screw for treating a condition of a spine of a patient, the orthopedic screw comprising: an elongate threaded cylindrical shaft to be twisted (e.g., rotated) into a threaded conduit of a body or housing of the tulip of the pedicle screw; optionally a tapered tip at a first end of the cylindrical shaft to facilitate insertion into the threaded conduit of the tulip, the tapered tip including a rod engagement surface to engage the rod and apply compressive force to secure the rod within the tulip; and a head at a second end of the cylindrical shaft, the head to be manipulated during tightening or loosening of the orthopedic screw to rotate the threaded cylindrical shaft into the threaded conduit of the tulip, the head comprising an eyelet to receive a tether therethrough, wherein each of the ends of the tether is to be secured at a point on the spine of the patient that is displaced from a point of securement of the pedicle screw, and wherein the eyelet is configured to apply a force (e.g., pull) on a middle portion of the tether to transfer the force to the tether to counter bending of the spine.

Example 12. An orthopedic system for treating a spinal condition, comprising: a rod; a tether; a set screw including: a cylindrical shaft, a first end of the cylindrical shaft configured to physically abut the rod and apply compressive force to the rod, a helical inclined plane winding around the cylindrical shaft and configured to engage and mate with a corresponding helical inclined plane, a head at a second end of the cylindrical shaft, the head to be manipulated during tightening or loosening of the set screw to rotate the cylindrical shaft, and an eyelet disposed at the head of the cylindrical shaft, the eyelet configured to receive and secure the tether therethrough, wherein the tether extends through the eyelet, a first end of the tether is secured at a first point on the vertebral column of the patient and a second end of the tether is secured at a second point on the vertebral column of the patient; a pedicle screw to be inserted into a pedicle of a vertebrae of a patient to be treated for a spinal condition, the pedicle screw including: a shaft with a plurality of male threads wrapping around the shaft, the shaft configured to be inserted into a vertebra of the patient, a tulip including a channel to receive the rod within the tulip and a conduit with a helical inclined plane configured to engage and mate with the helical inclined plane of the set screw and receive the first end of the cylindrical shaft within the conduit of the tulip to secure the rod within the tulip; and wherein, the eyelet exerts a force on the tether, which transfers the force to the first point on the vertebral column and the second point on the vertebral column to inhibit forward movement by a portion of the vertebral column.

Example 13. An orthopedic system for treating a spinal condition, comprising: a tulip to secure to a rod, the tulip comprising: a housing that includes: a rod channel to receive the rod therethrough; a threaded conduit of a clamping mechanism, which is to secure the rod within the rod channel, and optionally a pedicle screw physically attached to the tulip and configured to be inserted into a vertebrae of a patient and secure the tulip at a point of insertion of the pedicle screw; an orthopedic screw to secure the rod to the tulip, the orthopedic screw comprising: an elongate threaded cylindrical shaft to be rotated into the threaded conduit of the tulip housing to engage and mate with the threaded conduit of the clamping mechanism, optionally a tapered tip at a first end of the cylindrical shaft to facilitate insertion into the threaded conduit of the tulip, the tapered tip including a rod engagement surface to engage the rod and apply compressive force to secure the rod within the tulip; a head at a second end of the cylindrical shaft, the head to be manipulated to rotate the threaded cylindrical shaft into the threaded conduit of the tulip, the head comprising an eyelet to receive a tether therethrough, wherein each of a first end and a second end of the tether are secured at a portion of the spine of the patient that is displaced from a point of securement of the pedicle screw, and wherein the eyelet is configured to apply a pulling force on at least a portion of the tether to transfer the force to the tether to counter bending in at least a portion of the spine of the patient.

Example 14. A method of treating a patient for a spinal condition comprising: inserting a pedicle screw into a pedicle of a vertebra of a fused portion of a spinal column, the pedicle screw including a tulip to receive a rod; securing the rod within the tulip by inserting an eyelet set screw into a threaded conduit of the tulip and tightening the eyelet set screw to tighten a clamping mechanism on the rod; securing a first end of a tether to a non-fused portion (e.g., a next adjacent segment to a portion of fused portion) of the spinal column; extending a middle portion of a tether through an eyelet of the eyelet set screw; securing the second end of the tether to the non-fused portion of the spinal column, wherein the tether is tightened to apply a pulling force on at least a portion of the spinal column countering bending in at least a portion of the spinal column by transferring a force to the tether.

Recitation in the claims of the term "first" with respect to a feature or element does not necessarily imply the existence of a second or additional such feature or element. It will be apparent to those having reasonable skill in the art that changes may be made to the details of the above-described embodiments without departing from the underlying principles of the invention.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

It will be obvious to those having skill in the art that many changes may be made to the details of the above-described embodiments without departing from the underlying principles of the invention. The scope of the present inventions should, therefore, be determined only by the following claims.

What is claimed is:

1. An orthopedic system for treating a spinal condition, comprising:

a rod;

a tether;

a set screw including:

a cylindrical shaft, a first end of the cylindrical shaft configured to physically abut the rod and apply compressive force to the rod, a helical inclined plane winding around the cylindrical shaft and configured to engage with a corresponding helical inclined plane, a head at a second end of the cylindrical shaft, the head to be manipulated during tightening or loosening of the set screw to rotate the cylindrical shaft, and an eyelet disposed at the head of the cylindrical shaft, the eyelet configured to receive the tether therethrough to secure a first portion of the tether relative to a fused portion of a spinal column to be treated, wherein a second portion of the tether is configured to be secured to a non-fused portion of the spinal column to be treated; and a pedicle screw to be inserted into a pedicle of a vertebra of a fused portion of the spinal column to be treated, the pedicle screw including:

a shaft with a plurality of male threads wrapping around the shaft, the shaft configured to be inserted into the vertebra of the fused portion of the spinal column to be treated, and a tulip including a channel to receive the rod within the tulip and a conduit with a helical inclined plane configured to engage and mate with the helical inclined plane of the set screw and to receive the first end of the cylindrical shaft within the conduit of the tulip to secure the rod within the tulip.

2. The orthopedic system of claim 1, further comprising:

a second pedicle screw to be inserted into a pedicle of the vertebra of the non-fused portion of the spinal column to be treated, the pedicle screw including:

a shaft with a plurality of male threads wrapping around the shaft, the shaft configured to be inserted into the vertebra of the non-fused portion of the spinal column; and;

a head to be manipulated during tightening or loosening of the second pedicle screw to rotate the cylindrical shaft, and an eyelet disposed at the head of the cylindrical shaft to secure the second portion of the tether to the non-fused portion of the spinal column to be treated.

3. The orthopedic system of claim 1, further comprising:

a second set screw including:

a cylindrical shaft, a first end of the cylindrical shaft configured to be inserted into a corresponding pedicle screw, a helical inclined plane winding around the cylindrical shaft and configured to engage and mate with a corresponding helical inclined plane, a head at a second end of the cylindrical shaft, the head to be manipulated during tightening or loosening of the second set screw to rotate the cylindrical shaft, and an eyelet disposed at the head of the cylindrical shaft to secure a second portion of the tether; and a second pedicle screw to be inserted into a pedicle of a vertebra of a non-fused portion of the spinal column to be treated, the pedicle screw including:

a shaft with a plurality of male threads wrapping around the shaft, the shaft configured to be inserted into the vertebra of the non-fused portion of the spinal column; and a tulip including a conduit with a helical inclined plane configured to engage and mate with the helical inclined plane of the second set screw and to receive the first end of the cylindrical shaft within the conduit to secure the first end of the tether and the second end of the tether to the spinal column.

4. The orthopedic system of claim 1, wherein the tether extends through the eyelet of the set screw and a first end of the tether is to be secured at a first point on the non-fused portion of the spinal column to be treated and the second end of the tether is to be secured at a second point on the non-fused portion of the spinal column to be treated.

5. The orthopedic system of claim 1, wherein the eyelet of the set screw is further configured to receive and secure a second tether disposed through the eyelet.

6. The orthopedic system of claim 5, wherein the second tether is disposed substantially parallel to the spinal column.

7. The orthopedic system of claim 5, wherein the eyelet is further configured to provide a specific angle of orientation to the first tether.

8. The orthopedic system of claim 7, wherein the eyelet is further configured to provide a specific angle of orientation to the second tether.

9. The orthopedic system of claim 8, wherein the specific angle provided to the first tether is based on the specific angle provided to the second tether.

10. The orthopedic system of claim 8, wherein the specific angle of orientation of the first tether is 45 degrees.

11. The orthopedic system of claim 5, wherein the second tether is configured to be secured to a receiving eyelet at a third point on the spinal column that is displaced a third distance from a point of securement of the pedicle screw on the vertebrae of the patient.

12. The orthopedic system of claim 1, wherein the first tether is configured to be secured to a hole in a spinous process of a vertebra of the spinal column.

13. An orthopedic system for treating a spinal condition, comprising:

a tulip to secure to a rod, the tulip comprising:

a housing that includes:

a rod channel to receive the rod therethrough; and a threaded conduit of a clamping mechanism, which is to secure the rod within the rod channel;

an orthopedic screw to secure the rod to the tulip, the orthopedic screw comprising:

an elongate threaded cylindrical shaft to be rotated into the threaded conduit of the tulip housing to engage and mate with the threaded conduit of the clamping mechanism; and a head at a second end of the cylindrical shaft, the head to be manipulated to rotate the threaded cylindrical shaft into the threaded conduit of the tulip, the head comprising an eyelet to receive a tether therethrough to secure a first portion of the tether relative to a fused portion of a spinal column to be treated.

14. The orthopedic system of claim 13, further comprising:

a pedicle screw to be inserted into a pedicle of a vertebra of a non-fused portion of the spinal column to be treated, the pedicle screw including:

a shaft with a plurality of male threads wrapping around the shaft, the shaft configured to be inserted into the vertebra of the non-fused portion of the spinal column; and;

a head to be manipulated during tightening or loosening of the pedicle screw to rotate the cylindrical shaft, and an eyelet disposed at the head of the cylindrical shaft to secure the second portion of the tether to the non-fused portion of the spinal column to be treated.

15. The orthopedic system of claim 13, further comprising:

a pedicle screw to be inserted into a pedicle of a vertebra of a non-fused portion of the spinal column to be treated, the pedicle screw including:

a shaft with a plurality of male threads wrapping around the shaft, the shaft configured to be inserted into the vertebra of the non-fused portion of the spinal column; and a tulip including a conduit with a helical inclined plane; and a second orthopedic screw including:

a cylindrical shaft including a first end configured to be inserted into the pedicle screw, a helical inclined plane winding around the cylindrical shaft and configured to engage and mate with the helical inclined plane of the conduit of the tulip;

a head at a second end of the cylindrical shaft, the head to be manipulated during tightening or loosening of the second orthopedic screw to rotate the cylindrical shaft; and an eyelet disposed at the head of the second orthopedic screw to secure a second portion of the tether to the non-fused portion of the spinal column.

16. The orthopedic system of claim 13, wherein the tether extends through the eyelet of the orthopedic screw and a first end of the tether is to be secured at a first point on a non-fused portion of the spinal column to be treated and the second end of the tether is to be secured at a second point on the non-fused portion of the spinal column to be treated.

17. A method of treating a patient for a spinal condition comprising:

securing a rod and a tulip at a fused portion of a spinal column to be treated by:

inserting an eyelet set screw into a threaded conduit of the tulip, and tightening the eyelet set screw to tighten a clamping mechanism on the rod;

extending a first portion of a tether through an eyelet of the eyelet set screw to secure the tether at the fused portion of the spinal column; and securing a second portion of the tether at a non-fused portion of the spinal column.

18. The method of claim 17, further comprising:

tensioning the tether to apply a pulling force on at least a portion of the spinal column countering bending in at least a portion of the spinal column by transferring a force to the tether.

19. The method of claim 17, further comprising:

inserting a pedicle screw into a pedicle of a vertebra of the fused portion of the spinal column, the pedicle screw including the tulip.

20. The method of claim 17, wherein securing the second portion of the tether comprises:

securing a first end of a tether to the non-fused portion of the spinal column; and securing the second end of the tether to the non-fused portion of the spinal column.

21. The method of claim 17, wherein securing the second portion of the tether comprises:

inserting a pedicle screw into a pedicle of a vertebra of the non-fused portion of the spinal column, the pedicle screw including:

a shaft with a plurality of male threads winding around the shaft, the shaft configured to be inserted into the vertebra of the non-fused portion of the spinal column; and;

a head to be manipulated during tightening of the pedicle screw to rotate the shaft, and an eyelet disposed at the head of the shaft to secure the second portion of the tether to the non-fused portion of the spinal column.

22. The method of claim 17, wherein securing the second portion of the tether comprises:

inserting a pedicle screw into a pedicle of a vertebra of the non-fused portion of the spinal column, the pedicle screw including:

a shaft with a plurality of male threads wrapping around the shaft, the shaft configured to be inserted into a vertebra of the non-fused portion of the spinal column; and a tulip including a threaded conduit with a helical inclined plane;

inserting a second eyelet set screw into the threaded conduit of the tulip of the pedicle screw; and securing the second portion of the tether to an eyelet of the second eyelet set screw.

* * * * *